United States Patent [19]

Talley et al.

[11] Patent Number: 5,510,496

[45] Date of Patent: Apr. 23, 1996

[54] SUBSTITUTED PYRAZOLYL BENZENESULFONAMIDES

[75] Inventors: John J. Talley, St. Louis, Mo.; Thomas D. Penning, Elmhurst, Ill.; Paul W. Collins, Deerfield, Ill.; James W. Malecha, Libertyville, Ill.; Stephen R. Bertenshaw, Brentwood; Matthew J. Graneto, St. Louis, both of Mo.

[73] Assignee: G.D. Searle & Co., Chicago, Ill.

[21] Appl. No.: 456,441

[22] Filed: Jun. 1, 1995

Related U.S. Application Data

[62] Division of Ser. No. 160,594, Nov. 30, 1993, Pat. No. 5,466,823.

[51] Int. Cl.⁶ .................................................. C07D 231/12
[52] U.S. Cl. ...................... 548/365.7; 548/370.1; 548/370.4; 548/371.7; 548/372.1; 548/375.1; 548/376.1; 548/374.1; 548/377.1
[58] Field of Search .............................. 548/377.1, 365.7; 514/406

[56] References Cited

U.S. PATENT DOCUMENTS

| | | |
|---|---|---|
| 3,940,418 | 2/1976 | Hamilton . |
| 4,146,721 | 3/1979 | Rainer . |
| 5,134,142 | 7/1992 | Matsuo et al. . |
| 5,315,012 | 5/1994 | Connolly et al. . |

FOREIGN PATENT DOCUMENTS

| | | |
|---|---|---|
| 94/75753 | 12/1993 | Australia . |
| 347773 | 12/1989 | European Pat. Off. . |
| 477049 | 3/1992 | European Pat. Off. . |
| 554829 | 8/1993 | European Pat. Off. . |

OTHER PUBLICATIONS

R. Soliman et al, *J. Pharm. Sci.*, 76 626 (1987).
H. Mokhtar, *Pak. J. Sci. Ind. Res.*, 31, 762 (1988).
H. Mokhtar et al, *Pak. J. Sci. Ind. Res.*, 34, 9 (1991).
M. Cocco et al. Il. *Farmaco–Ed. Sci.*, 40, 272 (1985).
R. Soliman et al, *J. Pharm. Sci.*, 72, 1004 (1983).
H. Feid–Allah, *Pharmazie*, 36, 754 (1981).
R. Soliman et al, *J. Pharm. Sci.*, 70, 602 (1981).
Maybridge Chemical Co./Ryan Scientific Catalog, Compound No. BTB 06812. (No date available).
H. Mokhtar et al, *Pak J. Sci. Ind. Res.*, 33:30–46 (1990).
H. Mokhtar et al, *J. Chem. Soc. Pak.*, 10:414–424 (1988).
R. Soliman et al, *J. Pharm. Sci.*, 72:999–1004 (1983).
M.S. I. Makki et al, *Chem. Abstracts*, 121:11 (1994).
R. Hamilton, *J. Heterocyclic Chem.*, 13, 545 (1976).
M. Hashem et al, *J. Med. Chem.*, 19, 229 (1976).
H. Feid–Allah, *J. Heterocyclic Chem.*, 18, 1561 (1981).
H. Mokhtar et al, *Pharmazie*, 33, 649 (1978).
R. Soliman et al, *Pharmazie*, 33 (1978).

*Primary Examiner*—Robert W. Ramsuer
*Attorney, Agent, or Firm*—Joseph W. Bulock; J. Timothy Keane

[57] ABSTRACT

A class of pyrazolyl benzenesulfonamide compounds is described for use in treating inflammation and inflammation-related disorders. Compounds of particular interest are defined by Formula I:

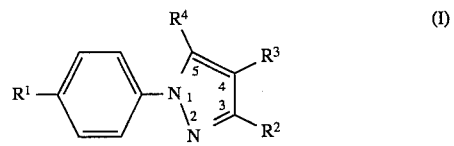

wherein $R^1$ is selected from sulfamyl, fluoro, chloro, methyl, hydroxyl, methoxy and trifluoromethyl: wherein $R^2$ is selected from hydrido, difluoromethyl, trifluoromethyl, amido, dichloromethyl, trichloromethyl, pentafluoroethyl, cyano, heptafluoropropyl, difluorochloromethyl, methoxycarbonyl, dichlorofluoromethyl, N-phenylamido, N-3-fluorophenyl) amido, 2-pyridylamido, N-(4-methylphenyl)amido, hydroxypropyl, N-(3-chlorophenyl)amido, N-(4-methoxyphenyl)amido, hydroxymethyl, hydroxyethyl, carboxylpropyl, carboxymethyl and carboxyethyl; wherein $R^3$ is selected from hydrido, methyl, triflouromethyl, fluoro, chloro and bromo; wherein $R^4$ is selected from phenyl, biphenyl, pyrazinyl, cyclohexyl, cyclohexenyl and thienyl; and wherein $R^4$ is optionally substituted at a substitutable position with one or more radicals selected from chloro, bromo, fluoro, methylthio, methylsulfonyl, morpholinyl, amino, methyl, ethyl, propyl, isopropyl, butyl, ethoxy, nitro, chloromethyl, trifluoromethoxy, trifluoroenhoxy, fluoromethyl, methoxy, difluoromethyl, trifluoromethyl, dichloromethyl, pentafluoroethyl, heptafluoropropyl, difluorochloromethyl, dichlorofluoromethyl, difluoroethyl, and difluoropropyl; or wherein $R^3$ and $R^4$ together form

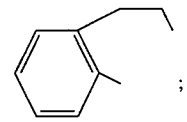

provided $R^2$ and $R^3$ are not both hydrido; or a pharmaceutically-acceptable salt thereof.

8 Claims, No Drawings

SUBSTITUTED PYRAZOLYL BENZENESULFONAMIDES

This is a divisional of U.S. application Ser. No. 08/160,594, filed Nov. 30, 1993 now U.S. Pat. No. 5,466,823.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIps) that are active in reducing the prostaglandin-induced pain and swelling associated with the inflammation process are also active in affecting other prostaglandin-regulated processes not associated with the inflammation process. Thus, use of high doses of most common NSAIps can produce severe side effects, including life threatening ulcers, that limit their therapeutic potential. An alternative to NSAIps is the use of corticosteroids, which have even more drastic side effects, especially when long term therapy is involved.

Pyrazoles have been described for use in the treatment of inflammation. U.S. Pat. No. 5,134,142 to Matsuo et al describes 1,5-diaryl pyrazoles, and specifically, 1-(4-fluorophenyl)-5-[40(methylsulfonyl)phenyl]-3-trifluoromethyl pyrazole, as having anti-inflammatory activity.

However pyrazolyl-benzenesulfonamides have not been described as having such activity. Certain substituted pyrazolyl-benzenesulfonamides have been described in the literature as synthetic intermediates. Specifically, 4-[5-(4-chlorophenyl)-3-phenyl-1H-pyrazol-1-yl]benzenesulfonamide has been prepared from a pyrazoline compound as an intermediate for compounds having hypoglycemic activity [R. Soliman et al, *J. Pharm, Sci.*, 76, 626 (1987)]. 4-[5-[2-(4-Bromophenyl)-2H-1,2,3-triazol-4-yl]-3-methyl-1H-pyrazol-1-yl]benzenesulfonamide has been prepared from a pyrazoline compound and described as potentially having hypoglycemic activity [H. Mokhtar, *Pak, J, Sci. Ind. Res.*, 31, 762 (1988)]. Similarly, 4-[4-bromo-5-[2-(4-chlorophenyl)-2H-1,2,3-triazol-4-yl]-3-methyl-1H-pyrazol-1-yl]benzenesulfonamide has been prepared [H. Mokhtar et al, *Pak. J. Sci. Ind. Res.* 34, 9 (1991)].

The phytotoxicity of pyrazole derivatives is described [M. Cocco et al, *Il. Farmaco-Ed. Sci.*, 40, 272 (1985)], specifically for 1-[4-(aminosulfonyl)phenyl]-5-phenyl-1H-pyrazole-3,4-dicarboxylic acid.

The use of 4-[3,4,5-trisubstituted-pyrazol-1-yl]benzenesulfonamides as intermediates for sulfonylurea anti-diabetes agents is described, and specifically, 1-[4-(aminosulfonyl)phenyl]-3-methyl-5-phenyl-1H-pyrazole-4-carboxylic acid [R. Soliman et al, *J. Pharm. Sci,*, 72, 1004 (1983)]. A series of 4-[3-substitutedmethyl-5-phenyl-1H-pyrazol-1-yl] benzenesulfonamides has been prepared as intermediates for anti-diabetes agents, and more specifically, 4-[3-methyl-5-phenyl-1H-pyrazol-1-yl]benzenesulfonamide [H. Feid-Allah, *Pharmazie*, 36, 754 (1981) ]. In addition, 1-(4-[aminosulfonyl]phenyl)-5-phenylpyrazole-3-carboxylic acid has been prepared from the above described 4-[3-methyl-5-phenyl-1H-pyrazol-1-yl]benzenesulfonamide compound [R. Soliman et al, *J. Pharm. Sci.*, 70, 602 (1981)].

DESCRIPTION OF THE INVENTION

A class of compounds useful in treating inflammation-related disorders is defined by Formula I:

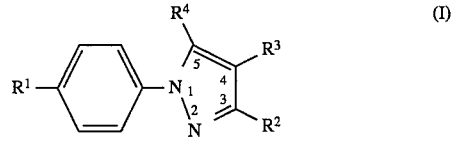

wherein $R^1$ is selected from sulfamyl, halo, alkyl, alkoxy, hydroxyl and haloalkyl; wherein $R^2$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl and heterocyclic; wherein $R^3$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl, heterocyclic, heterocycloalkyl and aralkyl; wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino; or wherein $R^3$ and $R^4$ together form

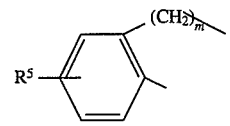

and m is 1 to 3, inclusive; and wherein $R^5$ is one or more radicals selected from halo, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro and acylamino; provided $R^2$ and $R^3$ are not identical radicals selected from hydrido, carboxyl and ethoxycarbonyl; further provided that $R^2$ cannot be carboxyl when $R^3$ is hydrido and when $R^4$ is phenyl; and further provided that $R^4$ is sulfamyl or N-alkylsulfamyl when $R^1$ is halo; or a pharmaceutically-acceptable salt thereof.

The phrase "further provided", as used in the above description, is intended to mean that the denoted proviso is not to be considered conjunctive with any of the other provisos.

Compounds of Formula I would be useful for the treatment of inflammation in a subject, and for treatment of other inflammation-associated disorders, such as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, systemic lupus erymhematosus, osteoarthritis and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis. Compounds of Formula I would be useful in treating inflammation in such diseases as vascular diseases, migraine headaches, periarteritis nodosa, thyroidiris, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like. The compounds are useful as anti-inflammatory agents, such as for the treatment of arthritis, with the additional benefit of having significantly less harmful side effects.

A preferred class of compounds consists of those compounds of Formula I wherein $R^2$ is selected from halo, haloalkyl, cyano, nitro, formyl, carboxyl, alkoxycarbonyl, carboxyalkyl, alkoxycarbonylalkyl, amidino, cyanoamidino, amido, amidoalkyl, N-monoalkylamido, N-monoarylamido, N,N-dialkylamido, N-alkyl-N-arylamido, alkylcarboxyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl and heterocyclic; wherein $R^3$ is hydrido; wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino; or wherein $R^3$ and $R^4$ together form

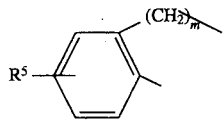

and m is 1 to 3, inclusive; and wherein $R^5$ is one or more radicals selected from halo, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydrido, hydroxyl, alkoxy, hydroxyalkyl, haloalkoxy, sulfamyl, N-alkylsulfamyl, amino, alkylamino, heterocyclic, nitro and acylamino; or a pharmaceutically-acceptable salt thereof.

A second preferred class of compounds consists of those compounds of Formula I wherein $R^1$ is sulfamyl; and wherein $R^3$ is hydrido; or a pharmaceutically-acceptable salt thereof.

A class of compounds of particular interest consists of those compounds of Formula I wherein $R^1$ is sulfamyl; wherein $R^2$ is selected from fluoro, chloro, bromo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, nitro, formyl, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amido, N-methylamido, N-ethylamido, N-isopropylamido, N-propylamido, N-butylamido, N-isobutylamido, N-tert-butylamido, N-pentylamido, N-cyclohexylamido, N-cyclopentylamido, N,N-dimethylamido, N-methyl-N-ethylamido, pyrrolidinoamido, piperidinoamido, N-phenylamido, N-(3-fluorophenyl)amido, N-(4-methylphenyl)amido, N-(3-chlorophenyl)amido, N-(4-methoxyphenyl)amido, 2-pyridylamido, N-methyl-N-phenylamido, N-methyl-N-pyridylamido, methylsulfonyl, phenylsulfonyl, N-phenylsulfamyl, N-methylsulfamyl, N-ethylsulfamyl, N-isopropylsulfamyl, N,N-dimethylsulfamyl, N-methyl-N-ethylsulfamyl, N-methyl-N-(3-chlorophenyl)sulfamyl, N-methyl-N-(2-pyridyl)sulfamyl, amidino, cyanoamidino, hydroxypropyl, hydroxymethyl, hydroxyethyl, carboxypropyl, carboxymethyl, carboxyethyl, tetrazolyl, imidazolyl and pyridyl; wherein $R^3$ is hydrido; wherein $R^4$ is selected from phenyl, naphthyl, biphenyl, cyclohexyl, cyclopentyl, cycloheptyl, 1-cyclohexenyl, 2-cyclohexenyl, 3-cyclohexenyl, 4-cyclohexenyl, 4-methylcyclohex-4-ene-1-yl, 1-cyclopentenyl, pyridyl, thienyl, thiazolyl, oxazolyl, furyl and pyrazinyl; wherein $R^4$ is optionally substituted at a substitutable position with one or more radicals selected from fluoro, chloro, bromo, methylthio, methylsulfinyl, cyano, carboxyl, amido, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, N-methylamido, N-ethylamido, N-isopropylamido, N-propylamido, N-butylamido, N-isobutylamido, N-tert-butylamido, N-pentylamido, N-cyclohexylamido, N-cyclopentylamido, N,N-dimethylamido, N-methyl-N-ethylamido, pyrrolidinoamido, piperidinoamido, N-phenylamido, N-(3-fluorophenyl)amido, N-(4-methylphenyl)amido, N-(3-chlorophenyl)amido, N-(4-methoxyphenyl)amido, 2-pyridylamido, N-methyl-N-phenylamido, N-methyl-N-pyridylamido, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, sulfamyl, methylsulfamyl, amino, nitro, methylamino, dimethylamino, formylamino, acetamino, trifluoroacetamino and morpholino; or a pharmaceutically-acceptable salt thereof.

A family of specific compounds of particular interest within Formula I consists of compounds and pharmaceutically-acceptable salts thereof as follows:

4-[5-(4-chlorophenyl)-3-(trifluoromethyl)-1H-pyrazol-1-yl]benzenesulfonamide;

4-[5-(4-bromophenyl)-3-(trifluoromethyl)-1H-pyrazol-1-yl]benzenesulfonamide;

4-[5-(3-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(2-chlorophenyl)-3-(trifluoromethyl)-1H-pyrazol-1-yl]benzenesulfonamide;

4-[5-(2-fluorophenyl)-3-(trifluoromethyl)-1H-pyrazol-1-yl]benzenesulfonamide;

4-[5-(4-trifluoromethylphenyl)-3-(trifluoromethyl)-1H-pyrazol-1-yl]benzenesulfonamide;

4-[5-(4-fluorophenyl)-3-(trifluoromethyl)-1H-pyrazol-1-yl]benzenesulfonamide;

4-[5-phenyl-3-(trifluoromethyl)-1H-pyrazol-1yl]benzenesulfonamide;

4-[5-(4-methoxyphenyl)-3-(trifluoromethyl)-1H-pyrazol-1-yl]benzenesulfonamide;

4-[5-(4-trifluoromethoxyphenyl)-3-(trifluoromethyl)-1H-pyrazol-1-yl]benzenesulfonamide;

4-[5-(4-bromophenyl)-3-(cyano)-1H-pyrazol-1-yl]benzenesulfonamide;

4-[5-(4-nitrophenyl)-3-(cyano)-1H-pyrazol-1-yl]benzenesulfonamide;

4-[5-(2-methylphenyl)-3-(trifluoromethyl)-1H-pyrazol-1-yl]benzenesulfonamide;

1-[4-(aminosulfonyl)phenyl]-5-(4-bromophenyl)-1H-pyrazole-3-carboxamide;

4-[5-(4-nitrophenyl)-3-(trifluoromethyl)-1H-pyrazol-1-yl]benzenesulfonamide;

4-[5-(4-aminophenyl)-3-(trifluoromethyl)-1H-pyrazol-1-yl]benzenesulfonamide;

methyl-1-[4-(aminosulfonyl)phenyl]-5-4-aminophenyl)-1H-pyrazole-3-carboxylate;

4-[5-(4-chlorophenyl)-3-(difluoromethyl)-1H-pyrazol-1-yl]benzenesulfonamide;

ethyl-1-[4-(aminosulfonyl)phenyl]-5-(4-chlorophenyl)-1H-pyrazole-3-carboxylate;

1-[4-(aminosulfonyl)phenyl]-5-(4-chlorophenyl)-1H-pyrazole-3-carboxylic acid;

4-[5-(2-pyrazinyl)-3-(trifluoromethyl)-1H-pyrazol-1-yl]benzenesulfonamide;

1-[4-(aminosulfonyl)phenyl]-5-(4-chlorophenyl)-1H-pyrazole-3-carboxamide;

4-[5-(4-[methylthio]phenyl)-3-(difluoromethyl)-1H-pyrazol-1-yl]benzenesulfonamide;

4-[5-(4-[methylsulfonyl]phenyl)-3-(difluoromethyl)-1H-pyrazol-1-yl]benzenesulfonamide;

4-[5-(2,4-[difluoro]phenyl)-3-(trifluoromethyl)-1H-pyrazol-1-yl]benzenesulfonamide;

4-[5-(2,6-[difluoro]phenyl)-3-(trifluoromethyl)-1H-pyrazol-1-yl]benzenesulfonamide;

4-[5-(4-cyanophenyl)-3-(trifluoromethyl)-1H-pyrazol-1-yl]benzenesulfonamide;

4-[5-(4-chlorophenyl)-3-(heptafluoropropyl)-1H-pyrazol-1-yl]benzenesulfonamide;

4-[5-(4-chlorophenyl)-3-(chloro-difluoromethyl)-1H-pyrazol-1-yl]benzenesulfonamide;

4-[5-(4-chlorophenyl)-3-(pentafluoroethyl)-1H-pyrazol-1-yl]benzenesulfonamide;

4-[5-(4-biphenyl)-3-(difluoromethyl)-1H-pyrazol-1-yl]benzenesulfonamide;

4-[5-(2-pyrazinyl)-3-(difluoromethyl)-1H-pyrazol-1-yl]benzenesulfonamide;

4-[5-(5-chloro-2-thienyl)-3-(difluoromethyl)-1H-pyrazol-1-yl]benzenesulfonamide;

4-[5-(4-(morpholino)phenyl)-3-(difluoromethyl)-1H-pyrazol-1-yl]benzenesulfonamide;

4-[5-(1-cyclohexenyl)-3-(difluoromethyl)-1H-pyrazol-1-yl]benzenesulfonamide;

4-[5-(1-cyclohexyl)-3-difluoromethyl)-1H-pyrazol-1-yl]benzenesulfonamide;

4-[5-(5-bromo-2-thienyl)-3-(trifluoromethyl)-1H-pyrazol-1-yl]benzenesulfonamide;

4-[5-(2-thienyl)-3-(difluoromethyl)-1H-pyrazol-1-yl]benzenesulfonamide;

4-[5-(4-[trifluoromethyl]phenyl)-3-(difluoromethyl)-1H-pyrazol-1-yl]benzenesulfonamide;

4-[5-(3,4-dichlorophenyl)-3-(trifluoromethyl)-1H-pyrazol-1-yl]benzenesulfonamide;

4-[5-(2,4-dichlorophenyl)-3-(trifluoromethyl)-1H-pyrazol-1-yl]benzenesulfonamide;

4-[5-phenyl-3-(3-hydroxypropyl)-1H-pyrazol-1-yl]benzenesulfonamide;

N-phenyl-1-[4-(aminosulfonyl)phenyl]-5-(4-fluorophenyl)-1H-pyrazole-3-carboxamide;

N-(4-methoxyphenyl)-1-[4-(aminosulfonyl)phenyl]-5-(4-fluorophenyl)-1H-pyrazole-3-carboxamide;

N-(3-fluorophenyl)-1-[4-(aminosulfonyl)phenyl]-5-(4-fluorophenyl)-1H-pyrazole-3-carboxamide;

N-(3-chlorophenyl)-1-[4-(aminosulfonyl)phenyl]-5-(4-chlorophenyl)-1H-pyrazole-3-carboxamide;

N-(4-methylphenyl)-1-[4-(aminosulfonyl)phenyl]-5-(4-chlorophenyl)-1H-pyrazole-3-carboxamide;

4-[5-(4-fluorophenyl)-3-(3-hydroxypropyl)-1H-pyrazol-1-yl]benzenesulfonamide;

1-[4-(aminosulfonyl)phenyl]-5-(4-fluorophenyl)-1H-pyrazole-3-propanoic acid;

methyl-1-[4-(aminosulfonyl)phenyl]-5-(4fluorophenyl)-1H-pyrazole-3-propanoate;

4-[5-(4-chlorophenyl)-3-(chloro)-1H-pyrazol-1-yl]benzenesulfonamide;

4-[5-(4-chlorophenyl)-3-(bromo)-1H-pyrazol-1-yl]benzenesulfonamide;

4-[5-(4-chlorophenyl)-3-(fluoro)-1H-pyrazol-1-yl]benzenesulfonamide;

4-[5-(4-chlorophenyl)-3-(fluoromethyl)-1H-pyrazol-1-yl]benzenesulfonamide;

4-[5-(4-chlorophenyl)-3-(chloromethyl)-1H-pyrazol-1-yl]benzenesulfonamide;

4-[5-(4-chlorophenyl)-3-(dichloromethyl)-1H-pyrazol-1-yl]benzenesulfonamide;

methyl-1-[4-(aminosulfonyl)phenyl]-5-(4-chlorophenyl)-1H-pyrazole-3-carboxylate;

4-[5-(4-chlorophenyl)-3-(cyano)-1H-pyrazol-1-yl]benzenesulfonamide;

N,N-dimethyl-1-[4-(aminosulfonyl)phenyl]-5-(4-chlorophenyl)-1H-pyrazole-3-carboxamide;

N-methyl-1-[4-(aminosulfonyl)phenyl]-5-(4-chlorophenyl)-1H-pyrazole-3-carboxamide;

N-methyl-N-ethyl-1-[4-(aminosulfonyl)phenyl]-5-(4-chlorophenyl)-1H-pyrazole-3-carboxamide;

N-phenyl-1-[4-(aminosulfonyl)phenyl]-5-(4-chlorophenyl)-1H-pyrazole-3-carboxamide;

N-methyl-N-phenyl-1-[4-(aminosulfonyl)phenyl]-5-(4chlorophenyl)-1H-pyrazole-3-carboxamide;

4-[5-(4-chlorophenyl)-3-(dichlorofluoromethyl)-1H-pyrazol-1-yl]benzenesulfonamide;

4-[5-(4-chlorophenyl)-3-(nitro)-1H-pyrazol-1-yl]benzenesulfonamide;

4-[5-(4-chlorophenyl)-3-(amidino)-1H-pyrazol-1-yl]benzenesulfonamide;

4-[5-(4-chlorophenyl)-3-(methylsulfonyl)-1H-pyrazol-1-yl]benzenesulfonamide;

4-[5-(4-chlorophenyl)-3-(N-methyl-aminosulfonyl)-1H-pyrazol-1-yl]benzenesulfonamide;

4-[5-(3,5-difluorophenyl)-3-(trifluoromethyl)-1H-pyrazol-1-yl]benzenesulfonamide;

4-[5-(2,4,6-trifluorophenyl)-3-(trifluoromethyl)-1H-pyrazol-1-yl]benzenesulfonamide;

4-[5-(2,6-dichlorophenyl)-3-(trifluoromethyl)-1H-pyrazol-1-yl]benzenesulfonamide;

4-[5-(2,4,6-trichlorophenyl)-3-(trifluoromethyl)-1H-pyrazol-1-yl]benzenesulfonamide;

4-[5-(2-methoxyphenyl)-3-(trifluoromethyl-1H-pyrazol-1-yl]benzenesulfonamide;

4-[5-(3-methoxyphenyl)-3-(trifluoromethyl-1H-pyrazol-1-yl]benzenesulfonamide;

4-[5-(3,5-dimethyl-4-methoxyphenyl)-3(trifluoromethyl)-1H-pyrazol-1-yl]benzenesulfonamide;

4-[5-(4-methoxy-3-methylphenyl)-3-(trifluoromethyl)-1H-pyrazol-1-yl]benzenesulfonamide;

4-[5-(2,4-dimethylphenyl)-3-(trifluoromethyl)-1H-pyrazol-1-yl]benzenesulfonamide;

4-[5-(3,4-dimethylphenyl)-3-(trifluoromethyl)-1H-pyrazol-1-yl]benzenesulfonamide;

4-[5-(3,4-dimethoxyphenyl)-3-(trifluoromethyl)-1H-pyrazol-1-yl]benzenesulfonamide;

4-[5-(3,4-methylenedioxyphenyl)-3-(trifluoromethyl)-1H-pyrazol-1-yl]benzenesulfonamide;

4-[5-(2-fluoro-4-methoxyphenyl)-3-(trifluoromethyl)-1H-pyrazol-1-yl]benzenesulfonamide;

4-[5-(3-fluoro-4-methoxyphenyl)-3-(trifluoromethyl)-1H-pyrazol-1-yl]benzenesulfonamide;

4-[5-(4- fluoro-2-methoxyphenyl)-3-(trifluoromethyl)-1H-pyrazol-1-yl]benzenesulfonamide;

4-[5-(2-chloro-4-methoxyphenyl)-3-(trifluoromethyl)-1H-pyrazol-1-yl]benzenesulfonamide;

4-[5-(4-chloro-2-methoxyphenyl)-3-(trifluoromethyl)-1H-pyrazol-1-yl]benzenesulfonamide;

4-[5-(2-methylthiophenyl)-3-(trifluoromethyl)-1H-pyrazol-1-yl]benzenesulfonamide;

4-[5-(3-methylthiophenyl)-3-(trifluoromethyl)-1H-pyrazol-1-yl]benzenesulfonamide;

4-[5-(4-methylthiophenyl)-3-(trifluoromethyl)-1H-pyrazol-1-yl]benzenesulfonamide;

4-[5-(2-methylsulfinylphenyl)-3-(trifluoromethyl)-1H-pyrazol-1-yl]benzenesulfonamide;

4-[5-(3-methylsulfinylphenyl)-3-(trifluoromethyl)-1H-pyrazol-1-yl]benzenesulfonamide;

4-[5-(4-methylsulfinylphenyl)-3-(trifluoromethyl)-1H-pyrazol-1-yl]benzenesulfonamide;

4-[5-(3-methylphenyl)-3-(trifluoromethyl)-1H-pyrazol-1-yl]benzenesulfonamide;

4-[5-(2-fluoro-4-methylphenyl)-3-(trifluoromethyl)-1H-pyrazol-1-yl]benzenesulfonamide;

4-[5-(4-fluoro-3-methylphenyl)-3-(trifluoromethyl)-1H-pyrazol-1-yl]benzenesulfonamide;

4-[5-(2-chloro-4-methylphenyl)-3-(trifluoromethyl)-1H-pyrazol-1-yl]benzenesulfonamide;

4-[5-(4-chloro-2-methylphenyl)-3-(trifluoromethyl)-1H-pyrazol-1-yl]benzenesulfonamide;

4-[5-(4-hydroxyphenyl)-3-(trifluoromethyl)-1H-pyrazol-1-yl]benzenesulfonamide;

4-[5-(3,4-dihydroxyphenyl)-3-(trifluoromethyl)-1H-pyrazol-1-yl]benzenesulfonamide;

4-[5-(biphenyl)-3-(trifluoromethyl)-1H-pyrazol-1yl]benzenesulfonamide;

4-[5-(5-indanyl)-3-(trifluoromethyl)-1H-pyrazol-1yl]benzenesulfonamide;

4-[5-(5-[2,3-dihydrobenzofuranyl])-3(trifluoromethyl)-1H-pyrazol-1-yl]benzenesulfonamide;

4-[5-(6-[1,2,3,4-tetrahydronapthyl])-3(trifluoromethyl)-1H-pyrazol-1-yl] benzenesulfonamide;

4-[5-(4-ethylphenyl)-3-(trifluoromethyl)-1H-pyrazol-1-yl]benzenesulfonamide;

4-[5-(4-isopropylphenyl)-3-(trifluoromethyl)-1H-pyrazol-1-yl]benzenesulfonamide;

4-[5-(6-methoxy-2-naphthyl)-3-(trifluoromethyl)-1H-pyrazol-1-yl]benzenesulfonamide;

4-[5-(2 -naphthyl)-3-(trifluoromethyl)-1H-pyrazol-1-yl]benzenesulfonamide;

4-[5-(4-[N-methylamino]phenyl)-3-(trifluoromethyl)-1H-pyrazol-1-yl]benzenesulfonamide;

4-[5-(4-[N,N-dimethylamino]phenyl)-3(trifluoromethyl)-1H-pyrazol-1-yl]benzenesulfonamide;

4-[5-(4-N-formylamino]phenyl)-3-(trifluoromethyl)-1H-pyrazol-1-yl]benzenesulfonamide;

4-[5-(4-[N-acetylamino]phenyl)-3-(trifluoromethyl)-1H-pyrazol-1-yl]benzenesulfonamide;

4-[5-(4-[N-methylaminosulfonyl]phenyl)-3(trifluoromethyl)-1H-pyrazol-1-yl]benzenesulfonamide;

4-[5-(4-hydroxymethylphenyl)-3-(trifluoromethyl)-1H-pyrazol-1-yl]benzenesulfonamide;

4-[5-(2-thienyl)-3-(trifluoromethyl)-1H-pyrazol-1-yl] benzenesulfonamide;

4-[5-(5-chloro-2-thienyl)-3-(trifluoromethyl)-1H-pyrazol-1-yl]benzenesulfonamide;

4-[5-(2-thiazolyl)-3-(trifluoromethyl)-1H-pyrazol-1-yl] benzenesulfonamide;

4-[5-(2-oxazolyl)-3-(trifluoromethyl)-1H-pyrazol-1-yl] benzenesulfonamide;

4-[5-(cyclohexyl)-3-(trifluoromethyl)-1H-pyrazol-1-yl] benzenesulfonamide;

4-[5-(cyclopentyl)-3-(trifluoromethyl)-1H-pyrazol-1-yl] benzenesulfonamide;

4-[5-(cycloheptyl)-3-(trifluoromethyl)-1H-pyrazol-1-yl] benzenesulfonamide;

4-[5-(1-cyclohexenyl)-3-(trifluoromethyl)-1H-pyrazol-1-yl]benzenesulfonamide;

4-[5-(1-cyclopentenyl)-3-(trifluoromethyl)-1H-pyrazol-1-yl]benzenesulfonamide;

4-[5-(2-furyl)-3-(trifluoromethyl)-1H-pyrazol-1-yl]benzenesulfonamide;

4-[5-(4-fluoro-2-methylphenyl)-3-(trifluoromethyl)-1H-pyrazol-1-yl]benzenesulfonamide;

4-[5-(4-chloro-3-methylphenyl) -3-(trifluoromethyl)-1H-pyrazol-1-yl]benzenesulfonamide;

4-[5-(2,5-dichlorophenyl)-3-(trifluoromethyl)-1H-pyrazol-1-yl]benzenesulfonamide;

4-[5-(4-ethoxyphenyl)-3-(trifluoromethyl)-1H-pyrazol-1-yl]benzenesulfonamide;

4-[5-(4-n-butoxyphenyl)-3-(trifluoromethyl)-1H-pyrazol-1-yl]benzenesulfonamide;

4-[5-(3-fluorophenyl)-3-(trifluoromethyl)-1H-pyrazol-1-yl]benzenesulfonamide;

4-[5-(4-[aminosulfonyl]phenyl)-3-(trifluoromethyl)-1H-pyrazol-1-yl]benzenesulfonamide;

4-[5-(2-pyridyl)-3-(trifluoromethyl)-1H-pyrazol-1-yl] benzenesulfonamide;

4-[5-(3-pyridyl)-3-(trifluoromethyl)-1H-pyrazol-1-yl]benzenesulfonamide;

4-[5-(6-methyl-3-pyridyl)-3-(trifluoromethyl)-1H-pyrazol-1-yl]benzenesulfonamide;

4-[5-(4-pyridyl)-3-(trifluoromethyl)-1H-pyrazol-1-yl]benzenesulfonamide;

4-[5-(4-aminophenyl)-3-(trifluoromethyl)-1H-pyrazol-1-yl]benzenesulfonamide;

4-[5-(4-acetamidophenyl)-3-(trifluoromethyl)-1H-pyrazol-1-yl]benzenesulfonamide;

4-[5-(4-[N-trifluoroacetamido]phenyl)-3(trifluoromethyl)-1H-pyrazol-1-yl]benzenesulfonamide;

4-[5-(4-fluorophenyl)-3-(imidazolyl)-1H-pyrazol-1-yl]benzenesulfonamide;

4-[5-(4-fluorophenyl)-3-(trichloromethyl)-1H-pyrazol-1-yl]benzenesulfonamide;

4-[5-(4-fluorophenyl)-3-(2-pyridyl)-1H-pyrazol-1-yl]benzenesulfonamide;

4-[1-[4-(aminosulfonyl)phenyl]-3-(trifluoromethyl)-1H-pyrazol-5-yl]benzoic acid;

methyl-4-[1-[4-(aminosulfonyl)phenyl]-3(trifluoromethyl)-1H-pyrazol-5-yl]benzoate;

4-[1-[4-(aminosulfonyl)phenyl]-3-(trifluoromethyl)-1H-pyrazol-5-yl]benzamide;

1-[4-(aminosulfonyl)phenyl]-5-(4-fluorophenyl)-1H-pyrazol-1-yl]-3-propanoic acid;

ethyl-1-[4-(aminosulfonyl)phenyl]-5-(4-chlorophenyl)-1H-pyrazole-3-carboxylate;

isopropyl-1-[4-(aminosulfonyl)phenyl]-5-(4chlorophenyl)-1H-pyrazole-3-carboxylate;

tert-butyl-1-[4-(aminosulfonyl)phenyl]-5-(4chlorophenyl)-1H-pyrazole-3-carboxylate;

propyl-1-[4-(aminosulfonyl)phenyl]-5-(4-chlorophenyl)-1H-pyrazole-3-carboxylate;

butyl-1-[4-(aminosulfonyl)phenyl]-5-(4-chlorophenyl)-1H-pyrazole-3-carboxylate;

isobutyl-1-[4-(aminosulfonyl)phenyl]-5-(4-chlorophenyl)-1H-pyrazole-3-carboxylate;

pentyl-1-[4-(aminosulfonyl)phenyl]-5-(4-chlorophenyl)-1H-pyrazole-3-carboxylate;

N-ethyl-1-[4-(aminosulfonyl)phenyl]-5-(4-chlorophenyl)-1H-pyrazole-3-carboxamide;

N-isopropyl-1-[4-(aminosulfonyl)phenyl]-5-(4-chlorophenyl)-1H-pyrazole-3-carboxamide;

N-propyl-1-[4-(aminosulfonyl)phenyl]-5-(4-chlorophenyl)-1H-pyrazole-3-carboxamide;

N-butyl-1-[4-(aminosulfonyl)phenyl]-5-(4-chlorophenyl)-1H-pyrazole-3-carboxamide;

N-isobutyl-1-[4-(aminosulfonyl)phenyl]-5-(4-chlorophenyl)-1H-pyrazole-3-carboxamide;

N-tert-butyl-1-[4-(aminosulfonyl)phenyl]-5-(4-chlorophenyl)-1H-pyrazole-3-carboxamide;

N-pentyl-1-[4-(aminosulfonyl)phenyl]-5-(4-chlorophenyl)-1H-pyrazole-3-carboxamide;

N-cyclohexyl-1-[4-(aminosulfonyl)phenyl]-5-(4-chlorophenyl)-1H-pyrazole-3-carboxamide;

N-cyclopentyl-1-[4-(aminosulfonyl)phenyl]-5-(4-chlorophenyl)-1H-pyrazole-3-carboxamide;

4-[5-(4-chlorophenyl)-3-(pyrrolidinocarboxamide)-1H-pyrazol-1-yl]benzenesulfonamide;

4-[5-(4-chlorophenyl)-3-(piperidinocarboxamide)-1H-pyrazol-1-yl]benzenesulfonamide;

N-(3-chlorophenyl)-1-[4-(aminosulfonyl)phenyl]-5-(4-chlorophenyl)-1H-pyrazole-3-carboxamide;

N-(2-pyridyl)-1-[4-(aminosulfonyl)phenyl]-5-(4chlorophenyl)-1H-pyrazole-3-carboxamide;

N-methyl-N-(3-chlorophenyl)-1-[4(aminosulfonyl) phenyl]-5-(4-chlorophenyl)-1H-pyrazole-3-carboxamide;

4-[5-(4-chlorophenyl)-3-(1,1-difluoroethyl)-1H-pyrazol-1-yl]benzenesulfonamide;

4-[5-(4-chlorophenyl)-3-(1,1-difluoropropyl)-1H-pyrazol-1-yl]benzenesulfonamide;

4-[5-(4-chlorophenyl)-3-(1,1-dichloroethyl)-1H-pyrazol-1-yl]benzenesulfonamide;

4-[5-(4-chlorophenyl)-3-(1,1-dichloropropyl)-1H-pyrazol-1-yl]benzenesulfonamide;

4-[5-(4-chlorophenyl)-3-(N-cyanoamidino)-1H-pyrazol-1-yl]benzenesulfonamide;

4-[5-(4-chlorophenyl)-3-(tetrazolyl)-1H-pyrazol-1-yl]benzenesulfonamide;

4-[5-(4-chlorophenyl)-3-(phenylsufonyl)-1H-pyrazol-1-yl]benzenesulfonamide;

4-[5-(4-chlorophenyl)-3-(N-phenylaminosulfonyl)-1H-pyrazol-1-yl]benzenesulfonamide;

4-[5-(4-chlorophenyl)-3-(N,N-dimethylaminosulfonyl)-1H-pyrazol-1-yl]benzenesulfonamide;

4-[5-(4-chlorophenyl)-3-(N-methyl-N-phenylaminosulfonyl)-1H-pyrazol-1-yl]benzenesulfonamide;

4-[5-(4-chlorophenyl)-3-(N-ethylaminosulfonyl)-1H-pyrazol-1-yl]benzenesulfonamide;

4-[5-(4-chlorophenyl)-3-(N-isopropylaminosulfonyl)-1H-pyrazol-1-yl]benzenesulfonamide;

4-[5-(4-chlorophenyl)-3-(N-methyl-N-ethylaminosulfonyl)-1H-pyrazol-1-yl]benzenesulfonamide;

4-[5-(4-chlorophenyl)-3-(N-methyl-N-(3-chlorophenyl)aminosulfonyl)-1H-pyrazol-1-yl] benzenesulfonamide;

4-[5-(4-chlorophenyl)-3-(N-methyl-N-(2pyridyl)aminosulfonyl)-1H-pyrazol-1-1] benzenesulfonamide;

4-[5-(2,3-difluorophenyl)-3-(trifluoromethyl)-1H-pyrazol-1-yl]benzenesulfonamide;

4-[5-(2,5-difluorophenyl)-3-(trifluoromethyl)-1H-pyrazol-1-yl]benzenesulfonamide;

4-[5-(2,3,4-trifluorophenyl)-3-(trifluoromethyl)-1H-pyrazol-1-yl]benzenesulfonamide;

4-[5-(3,4,5-trifluorophenyl)-3-(trifluoromethyl)-1H-pyrazol-1-yl]benzenesulfonamide;

4-[5-(2,4,5-trifluorophenyl)-3-(trifluoromethyl)-1H-pyrazol-1-yl]benzenesulfonamide;

4-[5-(2,5,6-trifluorophenyl)-3-trifluoromethyl)-1H-pyrazol-1-yl]benzenesulfonamide;

4-[5-(2,3,4,5-tetrafluorophenyl-3-trifluoromethyl)-1H-pyrazol-1-yl]benzenesulfonamide;

4-[5-(2,3,4,6-tetrafluorophenyl)-3-trifluoromethyl)-1H-pyrazol-1-yl]benzenesulfonamide;

4-[5-(2,3,5,6-tetrafluorophenyl)-3-trifluoromethyl)-1H-pyrazol-1-yl]benzenesulfonamide;

4-[5-(pentafluorophenyl)-3-(trifluoromethyl)-1H-pyrazol-1-yl]benzenesulfonamide;

4-[5-(2,3,4-trichlorophenyl)-3-(trifluoromethyl)-1H-pyrazol-1-yl]benzenesulfonamide 4-[5-(3,4,5-trichlorophenyl)-3-(trifluoromethyl)-1H-pyrazol-1-yl]benzenesulfonamide;

4-[5-(2,4,5-trichlorophenyl)-3-(trifluoromethyl)-1H-pyrazol-1-yl]benzenesulfonamide;

4-[5-(2,5,6-trichlorophenyl)-3-(trifluoromethyl)-1H-pyrazol-1-yl]benzenesulfonamide;

4-[5-(2,3,4,5-tetrachlorophenyl)-3-trifluoromethyl)-1H-pyrazol-1-yl]benzenesulfonamide;

4-[5-(2,3,4,6-tetrachlorophenyl)-3(trifluoromethyl)-1H-pyrazol-1-yl]benzenesulfonamide;

4-[5-(2,3,5,6-tetrachlorophenyl)-3(trifluoromethyl)-1H-pyrazol-1-yl]benzenesulfonamide;

4-[5-(pentachlorophenyl)-3-(trifluoromethyl)-1H-pyrazol-1 -yl]benzenesulfonamide;

4-[5-(4-tertbutylphenyl)-3-(trifluoromethyl)-1H-pyrazol-1-yl]benzenesulfonamide;

4-[5-(4-isobutylphenyl)-3-(trifluoromethyl)-1H-pyrazol-1-yl]benzenesulfonamide;

4-[5-(2-cyclohexenyl)-3-(trifluoromethyl)-1H-pyrazol-1-yl]benzenesulfonamide;

4-[5-(3-cyclohexenyl)-3-(trifluoromethyl)-1H-pyrazol-1-yl]benzenesulfonamide;

4-[5-(4-cyclohexenyl)-3-(trifluoromethyl)-1H-pyrazol-1-yl]benzenesulfonamide;

4-[5-(4-methylcyclohex-4-ene-1-yl)-3-(trifluoromethyl)-1H-pyrazol-1-yl] benzenesulfonamide;

4-[5-(5-chloro-2-furyl)-3-(trifluoromethyl)-1H-pyrazol-1-yl]benzenesulfonamide; and 4-[5-(5-bromo-2- furyl)-3-(trifluoromethyl)-1H-pyrazol-1-yl]benzenesulfonamide.

A third preferred class of compounds consists of those compounds of Formula I wherein $R^1$ is sulfamyl; wherein $R^3$ and $R^4$ together form

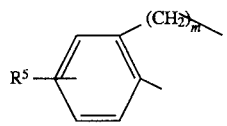

and m is 1 to 3, inclusive; and wherein $R^5$ is one or more radicals selected from halo, alkylthio, alkylsulfinyl, alkylsulfonyl, cyano, carboxyl, alkoxycarbonyl, amido, N-monoalkylamido, N-monoarylamido, alkyl, N,N-dialkylamido, N-alkyl-N-arylamido, haloalkyl, hydroxyl, alkoxy, hydroxyalkyl, haloalkoxy, sulfamyl, N-alkylsulfamyl, amino, alkylamino, heterocyclic, nitro and acylamino; or a pharmaceutically-acceptable salt thereof.

A class of compounds of particular interest consists of those compounds of Formula I wherein $R^1$ is sulfamyl; wherein $R^2$ is selected from fluoro, chloro, bromo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, nitro, formyl, carboxyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amido, N-methylamido, N-ethylamido, N-isopropylamido, N-propylamido, N-butylamido, N-isobutylamido, N-tert-butylamido, N-pentylamido, N-cyclohexylamido, N-cyclopentylamido, N,N-dimethylamido, N-methyl-N-ethylamido, pyrrolidinoamido, piperidinoamido, N-phenylamido, N-(3-fluorophenyl)amido, N-(4-methylphenyl)amido, N-(3-chlorophenyl)amido, N-(4-methoxyphenyl)amido, 2 -pyridylamido, N-methyl-N-phenylamido, N-methyl-N-pyridylamido, methylsulfonyl, phenylsulfonyl, N-phenylsulfamyl, N-methylsulfamyl, N-ethylsulfamyl, N-isopropylsulfamyl, N,N-dimethylsulfamyl, N-methyl-N-ethylsulfamyl, N-methyl-N-(3-chlorophenyl)sulfamyl, N-methyl-N-(2-pyridyl)sulfamyl, amidino, cyanoamidino, hydroxypropyl, hydroxymethyl, hydroxyethyl, carboxypropyl, carboxymethyl, carboxyethyl, tetrazolyl, imidazolyl and pyridyl; wherein $R^3$ and $R^4$ together form

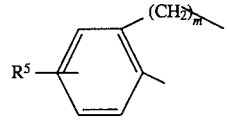

and m is 1 to 3, inclusive; and wherein $R^5$ is one or more radicals selected from fluoro, chloro, bromo, methylthio, methylsulfinyl, cyano, carboxyl, amido, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, N-methylamido, N-ethylamido, N-isopropylamido, N-propylamido, N-butylamido, N-isobutylamido, N-tertbutylamido, N-pentylamido, N-cyclohexylamido, N-cyclopentylamido, N,N-dimethylamido, N-methyl-N-ethylamido, pyrrolidinoamido, piperidinoamido, N-phenylamido, N-(3-fluorophenyl)amido, N-(4-methylphenyl)amido, N-(3-chlorophenyl)amido, N-(4methoxyphenyl)amido, 2 -pyridylamido, N-methyl -N-phenylamido, N-methyl-N-pyridylamido, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxyl, methoxy, methylenedioxy, ethoxy, propoxy, n-butoxy, trifluoromethoxy, hydroxymethyl, hydroxyethyl, hydroxypropyl, sulfamyl, methylsulfamyl, amino, nitro, methylamino, dimethylamino, formylamino, acetamino, trifluoroacetamino and morpholino; or a pharmaceutically-acceptable salt thereof.

A fourth preferred class of compounds consists of those compounds of Formula I wherein $R^1$ is selected from halo, alkyl, alkoxy, hydroxyl and haloalkyl; wherein $R^2$ is selected from haloalkyl; and wherein $R^4$ is phenyl substituted at a substitutable position with sulfamyl; or a pharmaceutically-acceptable salt thereof.

A class of compounds of particular interest consists of those compounds of Formula I wherein $R^1$ is selected from fluoro, chloro, bromo, fluoromethyl, difluoromethyl, trifluoromethyl, chloromethyl, dichloromethyl, trichloromethyl, pentafluoroethyl, heptafluoropropyl, difluorochloromenhyl, dichloropropyl, dichlorofluoromethyl, difluoroethyl, difluoropropyl, dichloroethyl, methyl, ethyl, propyl, hydroxyl, methoxy, ethoxy, propoxy and n-butoxy; wherein $R^2$ is selected from fluoromethyl, difluoromethyl, trifluoromethyl, chloromethyl, dichloromethyl, trichloromethyl, pentafluoroethyl, heptafluoropropyl, difluorochloromethyl, difluoroethyl, dichlorofluoromethyl, difluoropropyl, dichloroethyl and dichloropropyl; and wherein $R^3$ is hydrido; or a pharmaceutically-acceptable salt thereof.

A specific compound of particular interest within Formula I is 4-[1-(4-fluorophenyl)-3-(trifluoromethyl)-1H-pyrazol-5 -yl]benzenesulfonamide, or a pharmaceutically-acceptable salt thereof.

Within Formula I there is a fifth preferred class of compounds which consists of compounds wherein $R^1$ is sulfamyl; wherein $R^2$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl and heterocyclic; wherein $R^3$ is selected from halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N, N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl, heterocyclic, heterocycloalkyl and aralkyl; wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N,N-dialkylamino, heterocyclic, nitro and acylamino; or a pharmaceutically-acceptable salt thereof.

An even more preferred class contains compounds wherein $R^2$ is hydrido or haloalkyl; wherein $R^3$ is selected from alkyl, halo, carboxyalkyl, N-monoalkyl-N-hydroxyamido, N-monoalkyl-N-hydroxyamidoalkyl and N-monoalkylamido; and wherein $R^4$ is aryl optionally substituted at a substitutable position with halo; or a pharmaceutically-acceptable salt thereof.

A class of compounds of particular interest consist of those compounds wherein $R^1$ is sulfamyl; wherein $R^2$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; wherein $R^3$ is selected from fluoro, chloro, bromo, methyl, ethyl, propyl, isopropyl, butyl, N-methylamido, N-ethylamido, N-isopropylamido, N-propylamido, N-butylamido, N-isobutylamido, N-tert-butylamido, N-pentylamido, N-cyclohexylamido, N-cyclopentylamido, carboxypropyl, carboxymethyl, carboxyethyl, N-methyl-N-hydroxyamido, N-methyl-N-hydroxyamidomethyl, N-methyl-N-hydroxyamidoethyl and N-methyl-N-hydroxyamidopropyl; and wherein $R^4$ is phenyl optionally substituted at a substitutable position with one or more radicals selected from fluoro, chloro and bromo; or a pharmaceutically-acceptable salt thereof.

A family of specific compounds of particular interest consists of compounds and their pharmaceutically acceptable salts thereof as follows:

4-[5-(4-chlorophenyl)-3-(trifluoromethyl)-4-(methyl)-1H-pyrazol-1-yl]benzenesulfonamide;

4-[5-(4-chlorophenyl)-3-(trifluoromethyl)-4-chloro-1H-pyrazol-1-yl]benzenesulfonamide;

4-[5-(4-chlorophenyl)-3-(trifluoromethyl)-4-fluoro-1-H-pyrazol-1-yl]benzenesulfonamide;

4-[5-(4-chlorophenyl)-4-fluoro-1H-pyrazol-1-yl]benzenesulfonamide;

4-[5-(4-fluorophenyl)-3-(trifluoromethyl)-4-(n-propyl)-1H-pyrazol-1-yl]benzenesulfonamide;

4-[5-(4-chlorophenyl)-4-chloro-1H-pyrazol-1-yl]benzenesulfonamide;

N-methyl-N-hydroxy-1-[4-(aminosulfonyl)phenyl]-5-(4-fluorophenyl) -3-(trifluoromethyl)-1H-pyrazole-4ethanamide;

4-[5-(4-fluorophenyl)-3-(trifluoromethyl)-4-( phenylethyl)-1H -pyrazol-1-yl]benzenesulfonamide;

4-[5-(4-fluorophenyl)-3-(trifluoromethyl)-4-(2-[2-pyridyl]ethyl)-1 H-pyrazol-1-yl]benzenesulfonamide;

4-[5-(4-fluorophenyl)-3-(trifluoromethyl)-4-([N,N-dimethylamino ]ethyl)-1H-pyrazol-1-1]benzenesulfonamide;

4-[5-(4-fluorophenyl)-4-(trifluoromethyl)-1H-pyrazol-1-yl]benzenesulfonamide;

1-[4-(aminosulfonyl)phenyl]-5-(4-fluorophenyl)-3-chloro-1H-pyrazole-4-acetic acid;

1-[4-(aminosulfonyl)phenyl]-5-(4-fluorophenyl)-3-(trifluoromethyl)-1H-pyrazole-4-propanoic acid;

methyl-1-[4-(aminosulfonyl)phenyl]-5-(4-fluorophenyl)-3- trifluoromethyl)-1H-pyrazole-4 -propanoate;

1-[4-(aminosulfonyl)phenyl]-5-(4-fluorophenyl)-3-(trifluoromethyl)-1H-pyrazole-4-propanamide;

N-methyl-N-hydroxy-1-[4-(aminosulfonyl)phenyl]-5-(4-fluorophenyl )-3-(trifluoromethyl)-1H-pyrazole-4propanamide;

N-methyl-1-[4-(aminosulfonyl)phenyl]-5-(4-fluorophenyl)- 3-(trifluoromethyl)-1H-pyrazole-4-carboxamide; and 4-[5-(4-fluorophenyl)-3-(trifluoromethyl)-4-(methyl)-1H-pyrazol-1-yl]benzenesulfonamide.

Within Formula I there is a subclass of compounds of high interest represented by Formula II:

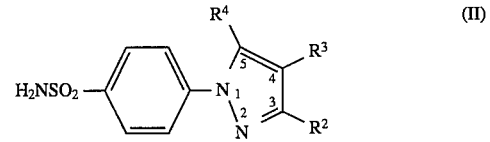

wherein $R^2$ is selected from hydrido, haloalkyl, alkoxycarbonyl, cyano, amido, arylamido, carboxyalkyl and hydroxyalkyl; wherein $R^3$ is hydrido or halo; and wherein $R^4$ is selected from aryl, cycloalkyl, cycloalkenyl and heterocyclic; wherein $R^4$ is optionally substituted at a substitutable position with one or more radicals selected from halo, alkylthio, alkylsulfonyl, cyano, nitro, haloalkyl, alkyl, hydrido, alkoxy, haloalkoxy, sulfamyl, heterocyclic and amino; or wherein $R^3$ and $R^4$ together form

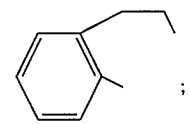

provided $R^2$ and $R^3$ are not both hydrido; or a pharmaceutically-acceptable salt thereof.

A preferred class of compounds consists of those compounds of Formula II wherein $R^2$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyano, methoxycarbonyl, ethoxycarbonyl, isopropoxycarbonyl, tertbutoxycarbonyl, propoxycarbonyl, butoxycarbonyl, isobutoxycarbonyl, pentoxycarbonyl, amido, N-phenylamido, N-(3-fluorophenyl)amido, N-(4-methylphenyl)amido, N-(3 -chlorophenyl)amido, N-(4-methoxyphenyl)amido, 2-pyridylamido, hydroxypropyl, hydroxymethyl, hydroxyethyl, carboxypropyl, carboxymethyl and carboxyethyl; wherein $R^3$ is selected from hydrido, fluoro, chloro, iodo and bromo; wherein $R^4$ is selected from phenyl, biphenyl, pyrazinyl, cyclohexyl, cyclohexenyl and thienyl; and wherein $R^4$ is optionally substituted at a substitutable position with one or more radicals selected from chloro, bromo, fluoro, methylthio, methylsulfonyl, morpholinyl, amino, nitro, methyl, ethyl, propyl, isopropyl, butyl, methoxy, ethoxy, propoxy, butoxy, trifluoromethoxy, trifluoroethoxy, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; or wherein $R^3$ and $R^4$ together form

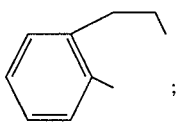

or a pharmaceutically-acceptable salt thereof.

A family of specific compounds of particular interest within Formula II consists of compounds and pharmaceutically-acceptable salts thereof as follows:

4-[5-(4-chlorophenyl)-3-(trifluoromethyl)-1H-pyrazol-1-yl]benzenesulfonamide;

4-[5-(4-chlorophenyl)-3-(trifluoromethyl)-4-chloro-1H-pyrazol-1-yl]benzenesulfonamide;

4-[5-(4-chlorophenyl)-4-chloro-1H-pyrazol-1-yl]benzenesulfonamide;

4-[5-(4-bromophenyl)-3-(trifluoromethyl)-1H-pyrazol-1-yl]benzenesulfonamide;

4-[5-(3-chlorophenyl)-3-(trifluoromethyl)-1H-pyrazol-1-yl]benzenesulfonamide;

4-[5-(4-methylphenyl)-3-(trifluoromethyl)-1H-pyrazol-1-yl]benzenesulfonamide;

4-[5-(2-chlorophenyl)-3-(trifluoromethyl)-1H-pyrazol-1-yl]benzenesulfonamide;

4-[5-(2-fluorophenyl)-3-(trifluoromethyl)-1H-pyrazol-1-yl]benzenesulfonamide;

4-[5-(4-trifluoromethylphenyl)-3-(trifluoromethyl)-1H-pyrazol-1-yl]benzenesulfonamide;

4-[5-(4-fluorophenyl)-3-(trifluoromethyl)-1H-pyrazol-1-yl]benzenesulfonamide;

4-[5-phenyl-3-(trifluoromethyl)-1H-pyrazol-1yl]benzenesulfonamide;

4-[5-(4-methoxyphenyl)-3-(trifluoromethyl-1H-pyrazol-1-yl]benzenesulfonamide;

4-[5-(4-trifluoromethoxyphenyl)-3-(trifluoromethyl)-1H-pyrazol-1-yl]benzenesulfonamide;

4-[5-(4-bromophenyl)-3-(cyano)-1H-pyrazol-1-yl]benzenesulfonamide;

4-[5-(4-nitrophenyl)-3-(cyano)-1H-pyrazol-1-yl]benzenesulfonamide;

4-[5-(2-methylphenyl)-3-(trifluoromethyl)-1H-pyrazol-1-yl]benzenesulfonamide;

4-[4-(aminosulfonyl)phenyl]-5-(4-bromophenyl)-1H-pyrazole-3-carboxamide;

4-[5-(4-nitrophenyl)-3-(trifluoromethyl)-1H-pyrazol-1-yl]benzenesulfonamide;

4-[5-(4-aminophenyl)-3-(trifluoromethyl)-1H-pyrazol-1-yl]benzenesulfonamide;

methyl-1-[4-(aminosulfonyl)phenyl]-5-(4-aminophenyl)-1H-pyrazole-3-carboxylate;

4-[5-(4-chlorophenyl)-3-(difluoromethyl)-1H-pyrazol-1-yl]benzenesulfonamide;

ethyl-1-[4-(aminosulfonyl)phenyl]-5-(4chlorophenyl)-1H-pyrazole-3-carboxylate;

4-[4-(aminosulfonyl)phenyl]-5-(4-chlorophenyl)-1H-pyrazole-3-carboxamide;

4-[5-(4-[methylthio]phenyl)-3-(difluoromethyl)-1H-pyrazol-1-yl]benzenesulfonamide;

4-[5-(2,4-[difluoro]phenyl)-3-(trifluoromethyl)-1H-pyrazol-1-yl]benzenesulfonamide;

4-[5-(2,6-[difluoro]phenyl)-3-(trifluoromethyl)-1H-pyrazol-1-yl]benzenesulfonamide;

4-[5-(4-chlorophenyl)-3-(heptafluoropropyl)-1H-pyrazol-1-yl]benzenesulfonamide;

4-[5-(4-chlorophenyl)-3-(chloro-difluoromethyl)-1H-pyrazol-1-yl]benzenesulfonamide;

4-[5-(4-chlorophenyl)-3-(pentafluoroethyl)-1H-pyrazol-1-yl]benzenesulfonamide;

4-[5-(4-biphenyl)-3-(difluoromethyl)-1H-pyrazol-1-yl]benzenesulfonamide;

4-[5-(5-chloro-2-thienyl)-3-(difluoromethyl)-1H-pyrazol-1-yl]benzenesulfonamide;

4-[5-(4-(morpholino)phenyl)-3-(difluoromethyl)-1H-pyrazol-1-yl]benzenesulfonamide;

4-[5-(1-cyclohexenyl)-3-(difluoromethyl)-1H-pyrazol-1-yl]benzenesulfonamide;

4-[5-(1-cyclohexyl)-3-(difluoromethyl)-1H-pyrazol-1-yl]benzenesulfonamide;

4-[5-(5-bromo-2-thienyl)-3-(trifluoromethyl)-1H-pyrazol-1-yl]benzenesulfonamide;

4-[5-(2-thienyl)-3-(difluoromethyl)-1H-pyrazol-1-yl]benzenesulfonamide;

4-[5-(4-[trifluoromethyl]phenyl)-3-(difluoromethyl)-1H-pyrazol-1-yl]benzenesulfonamide;

4-[5-(3,4-dichlorophenyl)-3-(trifluoromethyl)-1H-pyrazol-1-yl]benzenesulfonamide;

4-[5-(2,4-dichlorophenyl)-3-(trifluoromethyl)-1H-pyrazol-1-yl]benzenesulfonamide;

4-[5-phenyl-3-(3-hydroxypropyl)-1H-pyrazol-1-yl]benzenesulfonamide;

N-phenyl-1-[4-(aminosulfonyl)phenyl]-5-(4-fluorophenyl)- 1H-pyrazole-3-carboxamide;

N-[4-methoxyphenyl]-1-[4-(aminosulfonyl)phenyl]-5-(4-fluorophenyl)-1H -pyrazole-3 -carboxamide;

N-[3-fluorophenyl]-1-[4-(aminosulfonyl)phenyl]-5-(4-flurophenyl)-1H-pyrazole-3 -carboxamide;

N-[3-chlorophenyl]-1-[4-(aminosulfonyl)phenyl]-5-(4-fluorophenyl)-1H-pyrazole-3 -carboxamide;

N-[4-methylphenyl]-1-[4-(aminosulfonyl)phenyl]-5-(4-fluorophenyl)-1H-pyrazole-3 -carboxamide;

4-[4,5-dihydro-3-(trifluoromethyl)-1H-benz[g]indazol-1-yl]benzenesulfonamide;

4-[5-(4-fluorophenyl)-3-(3-hydroxypropyl)-1H-pyrazol-1-yl] benzenesulfonamide; and 1-[4-(aminosulfonyl)phenyl]-5-(4-fluorophenyl)-1H-pyrazole-3-propanoic acid.

Where the term "alkyl" is used, either alone or within other terms such as "haloalkyl" and "alkylsulfonyl", it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo radicals may have two or more of the same halo atoms or a combination of different halo radicals and polyhaloalkyl radicals may have more than two of the same halo atoms or a combination of different halo radicals. The term "hydroxyalkyl" embraces linear or branched alkyl radicals having one to about ten carbon atoms any one of which may be substituted with one or more hydroxyl radicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide "haloalkoxy" or "haloalkoxyalkyl" radicals. Examples of "alkoxy" radicals include methoxy, butoxy and trifluoromethoxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronapthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" embraces unsaturated heterocyclic radicals. Examples of unsaturated heterocyclic radicals, also termed "heteroaryl" radicals include thienyl, pyrryl, furyl, pyridyl, pyrimidyl, pyrazinyl, pyrazolyl, oxazolyl, isoxazolyl, imidazolyl, thiazolyl, pyranyl and tetrazolyl. The term also embraces radicals where heterocyclic radicals are fused with aryl radicals. Examples of such fused bicyclic radicals include benzofuran, benzothiophene, and the like. The term "sulfonyl", whether used alone or linked to other terms such as alkylsulfonyl, denotes respectively divalent radicals —SO$_2$—. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl" or "sulfonamidyl", whether alone or used with terms such as "N-alkylsulfamyl", "N-arylsulfamyl", "N,N-dialkylsulfamyl" and "N-alkyl-N-arylsulfamyl", denotes a sulfonyl radical substituted with an amine radical, forming a sulfonamide (—SO$_2$NH$_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted, respectively, with one aryl radical, and one alkyl and one aryl radical. The terms "carboxy" or "carboxyl", whether used alone or with other terms, such as "carboxyalkyl", denotes —CO$_2$H. The term "carboxyalkyl" embraces radicals having a carboxy radical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. An example of an "alkylcarbonyl" radical is CH$_3$—(C=O)—. The term "alkylcarbonylalkyl", denotes an alkyl radical substituted with an "alkylcarbonyl" radical. The term "alkoxycarbonyl" means a radical containing an alkoxy radical, as defined above, attached via an oxygen atom to a carbonyl (C=O) radical. Examples of such "alkoxycarbonyl" radicals include (CH$_3$)$_3$CO—C(=O)— and —(O=)C—OCH$_3$. The term "alkoxycarbonylalkyl" embraces radicals having "alkoxycarbonyl", as defined above substituted to an alkyl radical. Examples of such "alkoxycarbonylalkyl" radicals include (CH$_3$)$_3$COC(=O)(CH$_2$)$_2$— and —(CH$_2$)$_2$(=O)COCH$_3$. The term "amido" when used by itself or with other terms such as "amidoalkyl", "N-monoalkylamido", "N-monoarylamido", "N,N-dialkylamido", "N-alkyl-N-arylamido", "N-alkyl-N-hydroxyamido" and "N-alkyl-N-hydroxyamidoalkyl", embraces a carbonyl radical substituted with an amino radical. The terms "N-alkylamido" and "N,N-dialkylamido" denote amido groups which have been substituted with one alkyl radical and with two alkyl radicals, respectively. The terms "N-monoarylamido" and "N-alkyl-N-arylamido" denote amido radicals substituted, respectively, with one aryl radical, and one alkyl and one aryl radical. The term "N-alkyl-N-hydroxyamido" embraces amido radicals substituted with a hydroxyl radical and with an alkyl radical. The term "N-alkyl-N-hydroxyamidoalkyl" embraces alkyl radicals substituted with an N-alkyl-N-hydroxyamido radical. The term "amidoalkyl" embraces alkyl radicals substituted with amido radicals. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(=NH)—NH$_2$ radical. The term "cyanoamidino" denotes an —C(=N—CN)—NH$_2$ radical. The term "heterocycloalkyl" embraces heterocyclic-substituted alkyl radicals such as pyridylmethyl and thienylmethyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl and cycloheptyl. The term "cycloalkenyl" embraces unsaturated radicals having three to ten carbon atoms, such as cylopropenyl, cyclobutenyl, cyclopentenyl, cyclohexenyl and cycloheptenyl. The term "alkylthio" embraces radicals containing a linear or branched alkyl radical, of one to ten carbon atoms, attached to a divalent sulfur atom. An example of "alkylthio" is methylthio, (CH$_3$—S—). The term "alkylsulfinyl" embraces radicals containing a linear or branched alkyl radical, of one to ten carbon atoms, attached to a divalent —S(=O)— atom. The terms "N-alkylamino" and "N,N-dialkylamino" denote amino groups which have been substituted with one alkyl radical and with two alkyl radicals, respectively. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino (CH$_3$C(=O)—NH—).

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic sales made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I-IV, wherein the $R^1$–$R^5$ substituents are as defined for Formula I, above, except where further noted. Synthetic Scheme I shows the preparation of tetrasubstituted pyrazoles from starting material 1. In step 1 of synthetic Scheme I, the phenyl-methyl ketone (1) is treated with a base (preferably a lithium base such as lithium diisopropylamide or LiHMDS) and an alkylating reagent ($R^3X$, where X represents a leaving group such as tosyl) to give the substituted ketone (2). In step 2, the substituted ketone (2) is treated with base, such as sodium methoxide, and an ester, or ester equivalent, to give the intermediate diketone (3) in a procedure similar to that developed by Reid and Calvin, *J. Amer. Chem. Soc.*, 72, 2948–2952 (1950). In step 3, the diketone (3) is reacted with a substituted phenylhydrazine in acetic acid or an alcoholic solvent to give a mixture of pyrazoles (4) and (5). Separation of the desired pyrazole (4) can be achieved by chromatography or recrystallization.

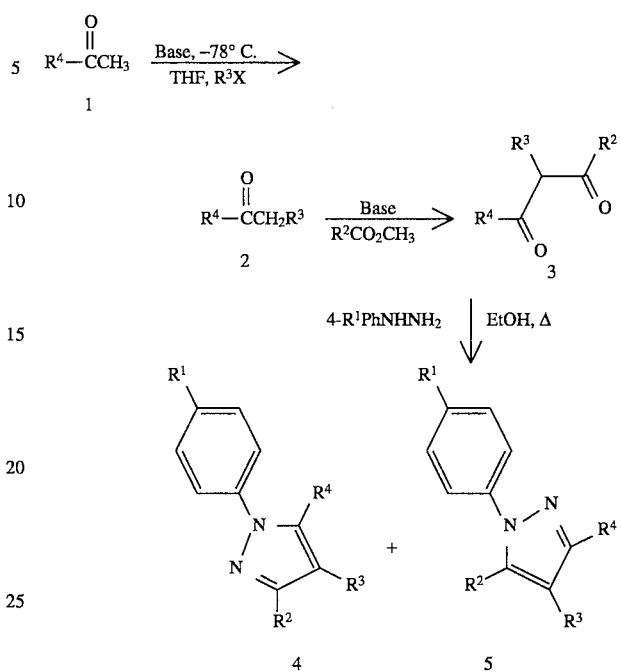

Synthetic Scheme II shows the preparation of compounds embraced by Formula I, where $R^3$ is a hydrogen atom. In step 1, ketone (1) is treated with a base, preferably NaOMe or NaH, and an ester, or ester equivalent, to form the intermediate diketone (6) which is used without further purification. In step 2, diketone (6) in an anhydrous protic solvent, such as absolute ethanol or acetic acid, is treated with the hydrochloride salt or the free base of a phenylhydrazine at reflux for 10 to 24 hours to afford a mixture of pyrazoles (7) and (8). Recrystallization from diethyl ether/hexane or chromatography affords (7), usually as a light yellow or tan solid.

Synthetic Scheme III shows the procedure for preparation of 4,5-dihydrobenz[g]indazole compounds embraced by Formula I. In step 1, ethyl trifluoroacetate is reacted with base, such as 25% sodium methoxide in a protic solvent, such as methanol, and a 1-tetralone derivative (9) to give the intermediate diketone (10). In step 2, the diketone (10) in an anhydrous protic solvent, such as absolute ethanol or acetic acid, is treated with the free base or hydrochloride salt of a phenylhydrazine at reflux for 24 hours to afford a mixture of pyrazoles (11) and (12). Recrystallization gives the 4,5-dihydro benz[g]indazolyl-benzenesulfonamide (11).

SCHEME III

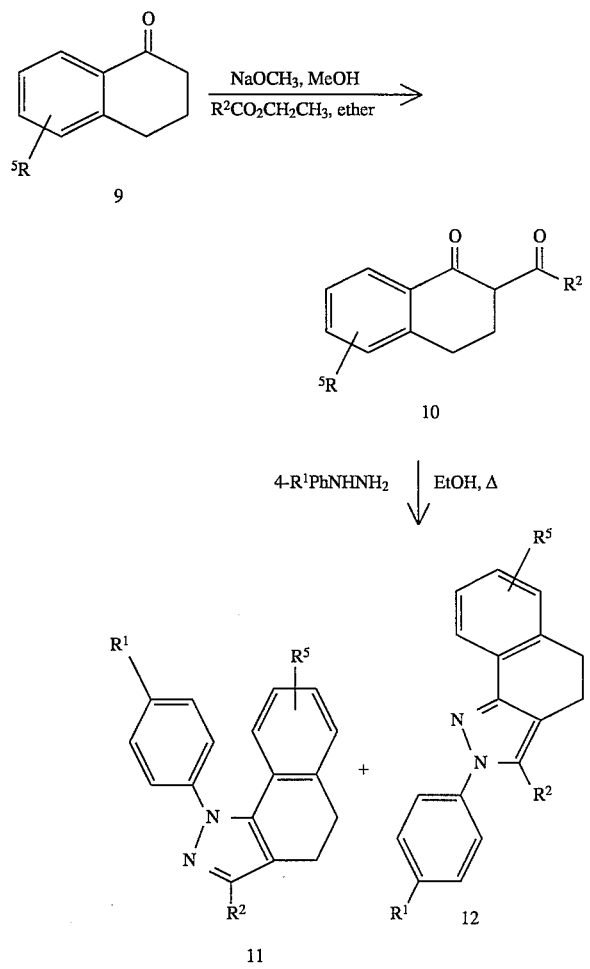

Synthetic Scheme IV shows the preparation of pyrazole compounds (13), where $R^3$ is chlorine, from the available pyrazole compounds (7), where $R^3$ is hydrogen. Chlorination results from passing a stream of chlorine gas at room temperature through a solution containing (7).

SCHEME IV

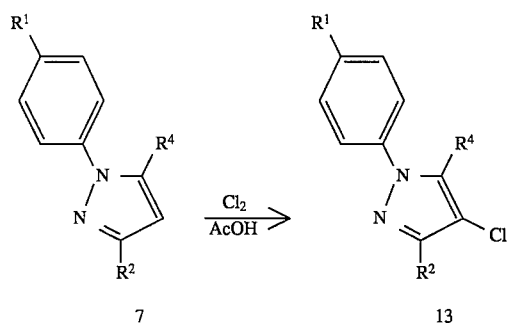

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

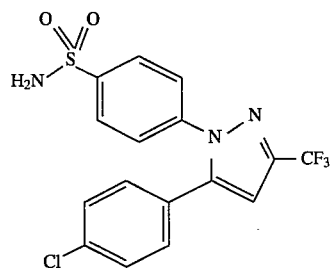

4-[5-(4-Chlorophenyl)-3-(trifluoromethyl)-1H-pyrazol-1-yl]benzenesulfonamide

Step 1: Preparation of 4,4,4-trifluoro-1-[4-(chloro)phenyl]-butane-1,3-dione.

Ethyl trifluoroacetate (23.52 g, 166 mmol) was placed in a 500 mL three-necked round bottom flask, and dissolved in methyl tert-butyl ether (75 mL). To the stirred solution was added 25 weight % sodium methoxide (40 mL, 177 mmol) via an addition funnel over a 2 minute period. Next 4'-chloroacetophenone (23.21 g, 150 mmol) was dissolved in methyl tert-butyl ether (20 mL), and added to the reaction dropwise over 5 minutes. After stirring overnight (15.75 hours), 3N HCl (70 mL) was added. The organic layer was collected, washed with brine (75 mL), dried over $MgSO_4$, filtered, and concentrated in vacuo to give a 35.09 g of yellow-orange solid. The solid was recrystallized from iso-octane to give 31.96 g, 85% of the dione, mp 66°–67° C.

Step 2: Preparation of 4-[5-(4-chlorophenyl)-3- (trifluoromethyl)-1H-pyrazol-1-yl]benzenesulfonamide.

4-Sulphonamidophenyl hydrazine hydrochloride (982 mg, 4.4 mmol 1.1 equivalent) was added to a stirred solution of 4,4,4-trifluoro-1-[4-(chloro)phenyl]-butane-1,3-dione (1.00 g, 4.0 mmol) in ethanol (50 mL). The reaction was heated to reflux and stirred for 20 hours. (HPLC area percent showed a 96:3 ratio of 4-[5-(4-chlorophenyl) -3-(trifluoromethyl)-1H-pyrazol-1-yl]benzenesulfonamide to its regioisomer (4-[3-(4-chlorophenyl)-5-(trifluoromethyl)-1H-pyrazol-1-yl]benzenesulfonamide). After cooling to room temperature, the reaction mixture was concentrated in vacuo. The residue was taken up in ethyl acetate and washed with water and brine and dried over $MgSO_4$, filtered, and concentrated in vacuo to give a light brown solid which was recrystallized from ethyl acetate and iso-octane to give the pyrazole 2, 1.28 g, 80% yield, mp 143°–145° C. HPLC showed that the purified material was a 99.5:0.5 mixture of 4-[5-(4-chlorophenyl)-3(trifluoromethyl)-1H-pyrazol- 1-yl]benzenesulfonamide to its regioisomer. $^1H$ NMR ($CDCl_3/CD_3OD$ 10/1) d 5.2 (s, 2H), 6.8 (s, 1H), 7.16 (d, J=8.5 Hz, 2H), 7.35 (d, J=8.5 Hz, 2H), 7.44 (d, J=8.66, 2H), 7.91 (d, J=8.66, 2H); $^{13}C$ NMR ($CDCl_3/CD_3OD$ 10/1) d 106.42 (d, J=0.03 Hz), 121.0 (q, J=276 Hz), 125.5, 126.9, 127.3,129.2, 130.1, 135.7, 141.5, 143.0, 143.9 (q, J=37 Hz), 144.0; $^{19}F$ NMR ($CDCl_3/CD_3OD$ 10/1) d−62.9. EI GC-MS M+=401.

The following compounds (Examples 1a to 1j) were obtained according to procedures similar to that exemplified in Example 1, with the substitution of the appropriate acetophenone.

(1a) 4-[5-(4-bromophenyl)-3-(trifluoromethyl)-1H-pyrazol-1-yl]benzenesulfonamide: off-white solid, mp 137°–139° C.; Anal. calc'd for $C_{16}H_{11}N_3O_2SBrF_3$: C, 43.07; H, 2.48; N, 9.42; Br, 17.91. Found: C, 43.01; H, 2.32; N, 9.39; Br, 17.62.

(1b) 4-[5-(3-chlorophenyl)-3-(trifluoromethyl)-1H-pyrazol-1-yl]benzenesulfonamide: yellow solid, mp 154°–155° C.; Anal. calc'd for $C_{16}H_{11}N_3O_2SClF_3$: C, 47.83; H, 2.76; N, 10.46; Cl, 8.82. Found: C, 47.61; H, 2.85; N, 10.31; Cl, 8.43.

(1c) 4-[5-(4-methylphenyl)-3-(trifluoromethyl)-1H- pyrazol-1-yl]benzenesulfonamide: yellow solid, mp 157°–159° C.; Anal. calc'd for $C_{17}H_{14}N_3O_2SF_3$: C, 53.54; H, 3.70; N, 11.02. Found: C, 53.17; H, 3.81; N, 10.90.

(1d) 4-[5-(2-chlorophenyl)-3-(trifluoromethyl)-1H-pyrazol-1-yl]benzenesulfonamide: white solid, mp 159°–160° C.; Anal. calc'd for $C_{16}H_{11}N_3O_2SClF_3$: C, 47.83; H, 2.76; N, 10.46. Found: C, 47.47; H, 2.65; N, 10.31.

(1e) 4-[5-(4-trifluoromethylphenyl)-3(trifluoromethyl)-1H-pyrazol -1-yl]benzenesulfonamide: yellow solid, mp 144°–145° C.; Anal. calc'd for $C_{17}H_{11}N_3O_2SF_6$: C, 46.90; H, 2.55; N, 9.65. Found: C, 46.98; H, 2.57; N, 9.61.

(1f) 4-[5-(4-fluorophenyl)-3-(trifluoromethyl)-1H- pyrazol-1-yl]benzenesulfonamide: mp 168°–169° C.; Anal. calc'd for $C_{16}H_{11}N_3O_2SF_4$: C, 49.87; H, 2.88; N, 10.90. Found: C, 49.83; H, 2.89; N, 10.86.

(1g) 4-[5-phenyl-3-(trifluoromethyl)-1H-pyrazol-1-yl] benzenesulfonamide: mp 164°–165° C.; Anal. calc'd for $C_{16}H_{12}N_3O_2SF_3$: C, 52.31; H, 3.29; N, 11.43. Found: C, 52.14; H, 3.07; N, 11.34.

(1h) 4-[5-(4-methoxyphenyl)-3-(trifluoromethyl)-1H-pyrazol-1-yl]benzenesulfonamide: mp 153°–154° C.; Anal. calc'd for $C_{17}H_{14}N_3O_3SF_3$: C, 51.38; H, 3.55; N, 10.57. Found: C, 51.00; H, 3.48; N, 10.24.

(1i) 4-[5-(4-trifluoromethoxyphenyl)-3( trifluoromethyl)-1H-pyrazol-1-yl]benzenesulfonamide: white solid, mp 101°–103° C.; Anal. calc'd for $C_{17}H_{11}N_3O_3SF_6$: C, 45.24; H, 2.46; N, 9.31. Found 45.22; H, 2.37; N, 9.29.

(1j) 4-[5-(2-methylphenyl)-3-(trifluoromethyl)-1H-pyrazol-1-yl]benzenesulfonamide: white solid, mp 126°–128° C. C; Anal. calc'd for $C_{17}H_{14}N_3O_2SF_3$: C, 53.54; H, 3.70; N, 11.02. Found: C, 53.52; H, 3.55; N, 11.06.

EXAMPLE 2

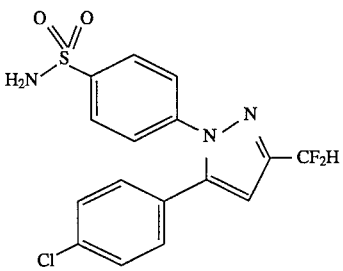

4-[5-(4-Chlorophenyl)-3-(difluoromethyl)-1H-1pyrazol- 1-yl]benzenesulfonamide

Step 1: Preparation of 4,4-difluoro-1-[4-(chloro)phenyl]-butane-1,3-dione.

Ethyl difluoroacetate (24.82 g, 200 mmol) was placed in a 500 mL three-necked round bottom flask, and dissolved in diethyl ether (200 mL). To the stirred solution was added 25 weight % sodium methoxide in methanol (48 mL, 210 mmol) via an addition funnel over a 2 minute period. Next, 4'-chloroacetophenone (25.94 g, 200 mmol) was dissolved in diethyl ether (50 mL), and added to the reaction dropwise over 5 minutes. After stirring overnight (18 hours), in HCl (250 mL) and ether (250 mL) were added. The organic layer was collected, washed with brine (250 mL), dried over $MgSO_4$, filtered, and concentrated in vacuo to give 46.3 g of a yellow solid. The solid was recrystallized from methylene chloride and iso-octane to give 31.96 g, 69% of the dione, mp 65°–66.5° C.

Step 2: Preparation of 4-[5-(4-chlorophenyl)-3- (difluoromethyl)-1H-pyrazol-1-yl]benzenesulfonamide 4-Sulphonamidophenyl hydrazine hydrochloride (1.45 g, 6.5 mmol 1.3 equivalent) and 4,4-difluoro-1-[4-(chloro)phenyl]-butane-1,3-dione (1.16 g, 5 mmol) were dissolved in ethanol (10 mL). The reaction was heated to reflux and stirred for 20 hours. After cooling to room temperature, the reaction mixture was concentrated in vacuo. The residue was taken up in ethyl acetate (100 mL) and washed with water (100 mL) and brine (100 mL), dried over $MgSO_4$, filtered, and concentrated in vacuo to give 1.97 g of a light brown solid which was recrystallized from ethanol and water to give 4-[5-(4-chlorophenyl )-3-(difluoromethyl)-1H-pyrazol-1-yl]benzenesulfonamide, 1.6 g, 83% yield, mp 185°–186° C.

EXAMPLE 3

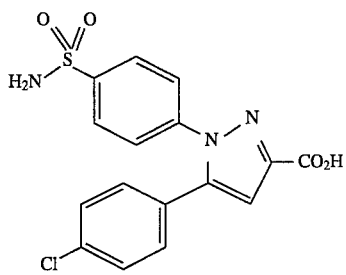

4-[4-(Aminosulfonyl)phenyl]-5-(4-chlorophenyl)-1H-pyrazole-3-carboxylate

Step 1: Preparation of methyl-4-[4-(chloro)phenyl]-2,4-dioxobutanoate.

Dimethyl oxalate (23.6 g, 200 mmol) was placed in a 500 mL three-necked round bottom flask, and dissolved in diethyl ether (200 mL). To the stirred solution was added 25 weight % sodium methoxide in methanol (48 mL, 210 mmol) via an addition funnel over a 2 minute period. Next, 4'-chloroacetophenone (27.94 g, 200 mmol) was dissolved in diethyl ether (50 mL), and added to the reaction dropwise over 3 minutes. After stirring overnight (18 hours), IN HCl (400 mL) and ethyl acetate (750 mL) were added. The organic layer was collected, washed with brine (350 mL), dried over $MgSO_4$, filtered, and concentrated in vacuo to give 45.7 g of a yellow solid. The solid was recrystallized from ethyl acetate and iso-octane to give 23 g, 48% of the diode, mp 108.5°–110.5° C.

Step 2: Preparation of 4-[4-(aminosulfonyl)phenyl]-5-(4-chloromethyl)-1H-pyrazole-3-carboxylate 4-Sulphonamidophenyl hydrazine hydrochloride (1.45 g, 6.5 mmol 1.3 equivalent) and methyl-4-[4-(chloro)phenyl]-2,4-dioxobutanoate (1.2 g, 5 mmol) were dissolved in ethanol (50 mL). The reaction was heated to reflux and stirred for 20 hours. After cooling to room temperature, the reaction mixture was concentrated in vacuo. The residue was taken up in ethyl acetate (200 mL) and washed with water (100 mL) and brine (100 mL), dried over $MgSO_4$, filtered and concentrated in vacuo to give 1.7 g of a light brown solid which was recrystallized from methanol and water to yield 1.6 g, 85% of a white solid. This material was dissolved in methanol (150 mL) and 3N NaOH (75 mL) and stirred at reflux for 3 hours. The methanol was removed in vacuo and the aqueous solution acidified with concentrated HCl. The product was then extracted into ethyl acetate (200 mL) which was washed with brine (100 mL), dried over $MgSO_4$ filtered and concentrated to give 4-[4-aminosulfonyl)phenyl]-5-(4-chlorophenyl)-1H-pyrazole-3-carboxylate, 1.4 g, 74%, mp 135° C. (decomposed).

EXAMPLE 4

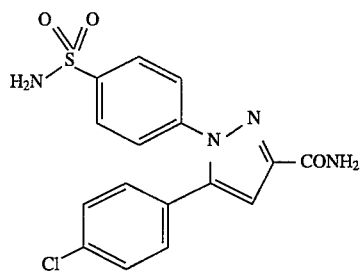

4-[4-(Aminosulfonyl)phenyl]-5-(4-chlorophenyl)-1H-pyrazole-3-carboxamide

4-[4-(Aminosulfonyl)phenyl]-5-(4-chlorophenyl)-1H-pyrazole-3-carboxylate (1.08 g, 2.86 mmol), HOBt (0.66 g, 4.3 mmol) and EDC (0.66 g, 3.4 mmol) were dissolved in dimethylformamide (DMF) (20 mL) and stirred at ambient temperature for 5 minutes. To this solution was added $NH_4OH$ (30%, 2.9 mL) and the reaction stirred for an additional 18 hours. This solution was then poured into ethyl acetate (200 mL) and 1N HCl (200 mL), shaken and separated. The organic layer was washed with saturated $NaHCO_3$ (150 mL) and brine (150 mL), dried over $MgSO_4$, filtered and concentrated to yield 0.9 g of a white solid which was recrystallized from ethyl acetate and isooctane to yield 4-[4-(aminosulfonyl)phenyl]-5-(4- chlorophenyl)-1H-pyrazole-3-carboxamide, 0.85 g, 79%, mp 108 °–110° C.

EXAMPLE 5

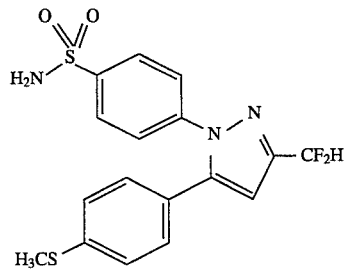

4-[5-(4-[Methylthio]phenyl)-3-(difluoromethyl)-1H-pyrazol-1-yl]benzenesulfonamide Step 1: Preparation of 4,4 -difluoro-1-[4-(methylthio)phenyl]-butane-1,3-dione Ethyl difluoroacetate (7.4 g, 60 mmol) was placed in a 500 mL three-necked round bottom flask, and dissolved in diethyl ether (60 mL). To the stirred solution was added 25 weight % sodium methoxide in methanol (14.4 mL, 63 mmol) via an addition funnel over a 2 minute period. Next, 4'-methylthio acetophenone (9.97 g, 60 mmol) was dissolved in diethyl ether (20 mL), and added to the reaction dropwise over 5 minutes. After stirring overnight (16 hours), in HCl (150 mL) and ether (150 mL) were added. The organic layer was collected, washed with brine (150 mL), dried over $MgSO_4$, filtered, and concentrated in vacuo to give 13.4 g of a light-brown solid. The solid was recrystallized from ethanol and water to give 9.9 g, 68% of the dione, mp 68°–70° C.

Step 2: Preparation of 4-[5-(4-[methylthio]phenyl)- 3-(difluoromethyl)-1H-pyrazol-1-yl]benzenesulfonamide 4-Sulphonamidophenyl hydrazine hydrochloride (1.34 g, 6 mmol 1.2 equivalent) and 4,4-difluoro-1-[4-(methylthio)phenyl]-butane-1,3-dione (1.22 g, 5 mmol) were dissolved in ethanol (50 mL). The reaction was beamed to reflux and stirred for 20 hours. After cooling to room temperature, the reaction mixture was concentrated in vacuo. The residue was taken up in ethyl acetate/200 mL) and washed with water (100 mL) and brine (100 mL), dried over $MgSO_4$, filtered and concentrated in vacuo to give 1.8 g of a light brown solid which was recrystallized from ethanol and water to yield 4-[5-(4-[methylthio]phenyl)-3-(difluoromethyl)- 1H-pyrazol-1yl]benzenesulfonamide as a white solid 1.14 g, 58%, mp 157°–158° C.

EXAMPLE 6

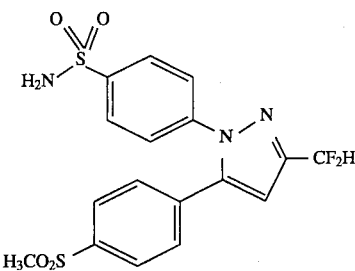

4-[5-(4-[Methylsulfonyl]phenyl)-3-(difluoromethyl)-1H-pyrazol-1-yl]benzenesulfonamide 4-[5-(4-[Methylthio]phenyl)-3-(difluoromethyl)-1H-pyrazol-1-yl]benzenesulfonamide (0.5 g, 1.27 mmol) was dissolved in methylene chloride (30 mL) and cooled to 0° C. To this solution was added m-chloroperoxybenzoic acid (MCPBA) (60%, 0.77 g, 2.7 mmol) and the solution was allowed to warm to room temperature while stirring for 18 hours. A solution of $Na_2S_2O_5$ (2 g) in $H_2O$ (25 mL) was added to the reaction mixture and the solution stirred vigorously for 0.5 hour. The layers were separated and the organic layer was washed with saturated $NaHCO_3$ (30 mL) and brine (30 mL), dried over $Na_2SO_4$ and concentrated to yield 4- [5-(4-[methylsulfonyl]phenyl)-3- (difluoromethyl)-1H-pyrazol-1-yl]benzenesulfonamide as a white solid 0.22 g, 40% mp=209°–210° C.

EXAMPLE 7

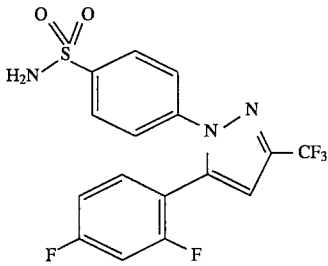

4-[5-(2,4-[Difluoro]phenyl)-3-(trifluoromethyl)-1H-pyrazol-1-yl]benzenesulfonamide Step 1: Preparation of 4,4,4-trifluoro-1-[2,4-(difluoro)phenyl]-butane-1,3-dione Ethyl trifluoroacetate (2.19 g, 15 mmol) was placed in a 100 mL round bottom flask, and dissolved in ether (10 mL). To the stirred solution was added 25 weight % sodium methoxide (3.35 g, 15 mmol) followed by 2',4'-difluoroacetophenone (2.11 g, 13 mmol). The reaction was stirred at room temperature overnight (15.8 hours), then poured into a separatory funnel and washed with 3N HCl (20 mL), brine (20 mL), dried over $MgSO_4$, and concentrated in vacuo to give a yellow oil which solidified after cooling in dry ice. (2.67 g, 78%). $^1$H NMR ($CDCl_3$) 300 MHz 15.00 (br s, 1H), 8.04 (m, 1H), 7.04 (m, 1H), 6.94 (m, 1H), 6.68 (s,1H) $^{19}$F NMR ($CDCl_3$) 300 MHz: –76.88 (s), –99.93 (m), –103.92 (m) M+Li 259.

Step 2: Preparation of 4-[5-(2,4-[difluoro]phenyl)- 3(trifluoromethyl)-1H-pyrazol-1-yl]benzenesulfonamide The 4-sulfonamidophenyl hydrazine hydrochloride (2.31 g, 10.3 mmol) was added to a stirred solution of the diketone (2.37 g, 9.4 mmol) in ethanol (10 mL). The reaction was heated to reflux and stirred overnight (15.5 hours). After cooling to room temperature, the ethanol was removed in vacuo. The residue was dissolved in ethyl acetate, washed two times with water, washed two times with brine, dried over $MgSO_4$, and concentrated in vacuo to give a brown foam which was recrystallized from ethyl acetate/isooctane to give the pyrazole as a tan solid (1.94 g, mp 127°–30° C., 51%). $^1$H NMR/$CDCl_3$ 300 MHz 7.91 (d, J=8.7 Hz, 2H), 7.45 (d, J=8.5 Hz, 2H), 7.28 (m, $^1$H), 6.96 (m, 1H), 6.87 (m, 1H), 6.81 (s, 1H) 5.03 (br s, 1H); $^{19}$F NMR ($CDCl_3$) 300 MHz: –62.87 (s), –105.60(m), –108.09 (m) M+H 404.

EXAMPLE 8

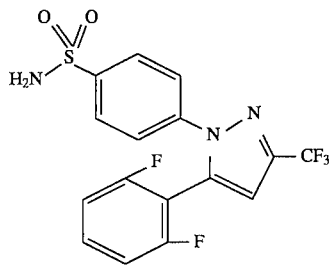

4- [5-(2,6-[Difluoro]phenyl)-3-(trifluoromethyl)-1H-pyrazol-1-yl]benzenesulfonamide Step 1: Preparation of 4,4,4-trifluoro-1-[2,6- (difluoro)phenyl]7butane-1,3-dione)

Ethyl trifluoroacetate (1.33 g, 9.3 mmol) was placed in a 100 mL round bottom flask, and dissolved in ether (10 mL). To the stirred solution was added 25 weight % sodium methoxide (2.11 g, 9.8 mmol) followed by 2',6'-difluoroacetophenone (1.32 g, 8.5 mmol). The reaction was stirred at room temperature overnight (15.8 hours), then poured into a separatory funnel and washed with in HCl (20 mL), brine (20 mL), dried over $HgSO_4$, and concentrated in vacuo to give the diketone as a white solid (1.68 g, mp 40°–44° C., 79%). $^1$H NMR ($CDCl_3$) 300 HHz 14.0 (br s, 1H), 7.49 (m, 1H), 7.02 (m, 2H), 6.36 (s, 1H); $^{19}$F NMR ($CDCl_3$) 300 MHz: –76.78 (s), –109.77 (s) M+H 253.

Step 2: Preparation of 4-[5-(2,6-[difluoro]phenyl)-3-(trifluoromethyl)-1H-pyrazol- 1-yl]benzenesulfonamide The 4-sulfonamidophenyl hydrazine hydrochloride (1.39 g, 6.2 mmol) was added to a stirred solution of the diketone/ 1.43 g, 5.7 mmol) in ethanol (10 mL). The reaction was heated to reflux and stirred overnight (15.75 hours). The ethanol was removed in vacuo, and the residue was dissolved in ethyl acetate, washed two times with water, washed two times with brine, dried over MgSO₄, and concentrated in vacuo to give a brown solid (1.97 g) which was recrystallized from ethyl acetate/isooctane to give the pyrazole as a white solid (1.00 g, mp 178°–80° C., 44%). ¹H NMR (acetone d⁶) 300 MHz 7.97 (d, J=8.9 Hz, 2H), 7.62 (m, 1H), 7.61 (d, J=8.9 Hz, 2H), 7.21 (s,1H), 7.16 (t, J=8.5 Hz, 2H), 6.75 (br s, 2H); ¹⁹F NMR (acetone d⁶) 300 MHz: −63.26 (s), −112.17(s) M+H 404.

EXAMPLE 9

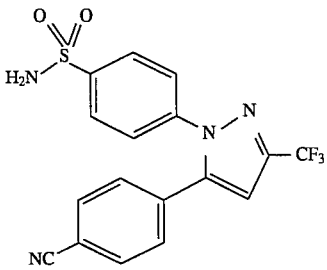

4-[5-(4-Cyanophenyl)-3-(trifluoromethyl)-1H-pyrazol-1-yl]benzenesulfonamide

Step 1: Preparation of 4,4,4-trifluoro-1-[4-(cyano)phenyl]-butane-1,3-dione

Ethyl trifluoroacetate (5.91 g, 41.6 mmol) was placed in a 100 mL round bottom flask, and dissolved in ether (30 mL). To the stirred solution was added 25 weight % sodium methoxide (9.02 g, 41.7 mmol) followed by 4-acetylbenzonitrile (5.46 g, 37.6 mmol). The reaction was stirred at room temperature for 4.2 hours, then treated with 1N HCl (50 mL). The reaction mixture was filtered to collect the diketone as a white solid (3.63 g). The filtrate was extracted with ethyl acetate, washed with brine (20 mL), dried over MgSO₄, and concentrated in vacuo, and recrystallized from methylene chloride to give an additional 1.21 g (13%) of the diketone. (4.84 g, mp 124°–28° C., 53% ). ¹H NMR (CDCl₃) 300 MHz 8.04 <d, J=8.5 Hz, 2H), 7.81 (d, J=8.5 Hz, 2H), 6.59 (s, 1H); ¹⁹F NMR (CDCl₃) 300 MHz: −77.12 (s); M+H 242.

Step 2: Preparation of 4-[5-(4-cyanophenyl)-3-(trifluoromethyl)-1H-pyrazol-1-yl]benzenesulfonamide The 4-sulfonamidophenyl hydrazine hydrochloride (0.57 g, 2.5 mmol) was added to a stirred solution of the diketone (0.54 g, 2.2 mmol) in ethanol (10 mL). The reaction was heated to reflux and stirred for 5.5 hours. The reaction mixture was filtered to remove the insoluble excess hydrazine and the ethanol was removed in vacuo. The residue was dissolved in ethyl acetate, washed two times with water, washed once with brine, dried over MgSO₄, and concentrated in vacuo to give a yellow solid which was recrystallized from ethyl acetate/isooctane give the pyrazole as a yellow solid (0.52 g, mp 196°–97.5° C., 59% ). ¹H NMR (CDCl₃) 300 MHz 7.95 (d, J=8.8 Hz, 2H), 7.67 (d, J=8.5 Hz, 2H), 7.47 (d, J=8.8 Hz, 2H), 7.38 (d, J=8.5 Hz, 2H), 6.87 (s, 1H), 4.90 (br s, 2H); ¹⁹F NMR (CDCl₃) 300 MHz: −62.97 (s) ; M+H 393.

EXAMPLE 10

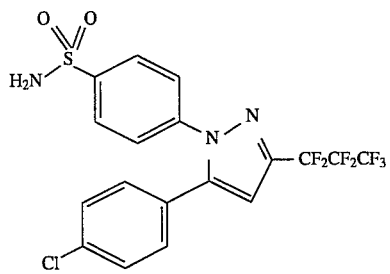

4-[5-(4-Chlorophenyl)-3-(heptafluoropropyl)-1H-pyrazol-1-yl]benzenesulfonamide

Ethyl heptafluorobutyrate (5.23 g, 21.6 mmol) was placed in a 100 mL round bottom flask, and dissolved in ether (20 mL). To the stirred solution was added 25 weight % sodium methoxide (4.85 g, 22.4 mmol) followed by 4-chloroacetophenone (3.04 g, 19.7 mmol). The reaction was stirred at room temperature overnight (15.9 hours) and treated with 3N HCl (17 mL). The organic layer was collected, washed with brine, dried over MgSO₄, concentrated in vacuo, and recrystallized from isooctane to give the diketone as a white solid (4.27 g, mp 27°–30° C., 62%). ¹H NMR (CDCl₃) 300 MHz 15.20 (br s, 1H), 7.89 (d, J=8.7 Hz, 2H), 7.51 (d, J=8.7 Hz, 2H), 6.58 (S, 1H); ¹⁹F NMR (CDCl₃) 100 MHz: −80.94 (t), −121.31 (t), −127.17 (s); M+H 351.

Step 2: Preparation of 4-[5-(4-chlorophenyl)-3-(heptafluoropropyl)-1H-pyrazol-1-yl]benzenesulfonamide The 4-sulfonamidophenyl hydrazine hydrochloride (290 mg, 1.30 mmol) was added to a stirred solution of the diketone (400 mg, 1.14 mmol) in ethanol (5 mL). The reaction was heated to reflux and stirred overnight (23.8 hours). The ethanol was removed in vacuo, and the residue was dissolved in ethyl acetate, washed with water and brine, dried over MgSO₄, and concentrated in vacuo to give a white solid which was passed through a column of silica gel with ethyl acetate/hexane (40%) and recrystallized from ethyl acetate/isooctane to give the pyrazole as a white solid (0.24 g, mp 168°–71° C., 42%). ¹H NMR (CDCl₃) 300 MHz 7.90 (d, J=8.7 Hz, 2H), 7.45 (d, J=8.7 Hz, 2H), 7.34 (d, J=8.5 Hz, 2H), 7.19 (d, J=8.5 Hz, 2H), 6.79 (s, 1 H), 5.20 (br s, 2H); ¹⁹F NMR (CDCl₃) 300 MHz: −80.48 (t), −111.54 (t), −127.07 (s).

EXAMPLE 11

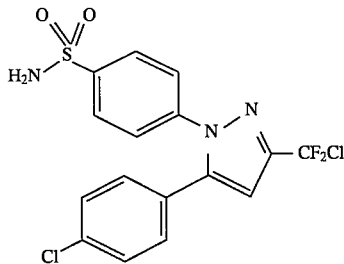

4-[5-(4-Chlorophenyl)-3-(chloro-difluoromethyl)-1H-pyrazol-1-yl]benzenesulfonamide Step 1: Preparation of 4-chloro-4,4-difluoro-1-(4-(chloro)phenyl]-butane-1,3-dione Methyl 2-chloro-2,2-difluoroacetate (4.20 g, 29 mmol) was placed in a 100 mL round bottom flask, and dissolved in ether (10 mL). To the stirred solution was added 25 weight % sodium methoxide (6.37 g, 29 mmol) followed by 4'-chloroacetophenone (4.10 g, 26.5 mmol). The reaction was stirred at room temperature overnight (20.4 hours), then poured into a separatory funnel and washed with 3N HCl (15 mL), brine (20 mL), dried over MgSO$_4$, and concentrated in vacuo and recrystallized from isooctane to give the diketone as a yellow solid (3.78 g, mp 53°–55° C., 53%). $^1$H NMR (CDCl$_3$) 300 MHz 14.80 (br s, 1H), 7.87 (d, J=8.7 Hz, 2H), 7.50 (d, J=8.7 Hz, 2H), 6.49 (S, 1H); $^{19}$F NMR (CDCl$_3$) 300 MHz: –66.03 (s); M+267.

Step 2: Preparation of 4-[5- (4-chlorophenyl)-3-(chlorodifluoromethyl)-1H-pyrazol-1-yl] benzenesulfonamide The 4-sulfonamidophenyl hydrazine hydrochloride (1.39 g, 6.2 mmol) was added to a stirred solution of the diketone (1.43 g, 5.7 mmol) in ethanol (10 mL). The reaction was heated to reflux and stirred overnight (15.75 hours). The ethanol was removed in vacuo, and the residue was dissolved in ethyl acetate, washed with water and brine, dried over MgSO$_4$, and concentrated in vacuo to give a white solid which was recrystallized from ethyl acetate/isooctane to give the pyrazole as a white solid (0.32 g, mp 130°–33° C., 41%). $^1$H NMR (CDCl$_3$) 300 MHz 7.90 (d, J=8.9 Hz, 2H), 7.47 (d, J=8.7 Hz, 2H}, 7.35 (d, J=8.5 Hz, 2H), 7.19 (d, J=8.7 Hz, 2H), 6.76 (s, 1 H), 5.13 (br s, 2H); $^{19}$F NMR (CDCl$_3$) 300 MHz: –48.44 (s); M+ 417/419.

EXAMPLE 12

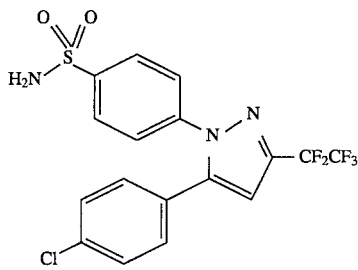

4-[5-(4-Chlorophenyl)-3-(pentafluoroethyl)-1H-pyrazol-1-yl]benzenesulfonamide

Step 1: Preparation of 4,4,5,5,5-pentafluoro-1-[4-chloro)phenyl]-pentane-1,3-dione, Ethyl Pentafluoropropionate (6.31 g, 32.8 mmol) was placed in a 100 mL round bottom flask, and dissolved in ether (15 mL). To the stirred solution was added 25 weight % sodium methoxide (7.90 g, 36.6 mmol) followed by 4'-chloroacetophenone (4.60 g, 29.8 mmol). The reaction was stirred at room temperature overnight (20.1 hours), then poured into a separatory funnel and washed with 3N HCl (20 mL), brine (20 mL), dried over MgSO$_4$, and concentrated in vacuo to give the diketone as a yellow powder which was recrystallized from isooctane to give yellow platelets. (7.07 g, mp 74°–77° C., 79%). $^1$H NMR (CDCl$_3$) 300 MHz 15.20 (br s, 1H), 7.88 (d, J=8.9 Hz, 2H), 7.51 (d, J=8.9 Hz, 2H), 6.60 (S, 1H); $^{19}$F NMR (CDCl$_3$) 300 MHz: –82.97 (t,J=2.2 Hz), –124.23 (s); M+H 301.

Step 2: Preparation of 4-[5-(4-chlorophenyl)-3- (pentafluoroethyl)-1H-pyrazol-1-yl]benzenesulfonamide The 4-sulfonamidophenyl hydrazine hydrochloride (1.39 g, 6.2 mmol) was added to a stirred solution of the diketone < 1.43 g, 5.7 mmol ) in ethanol (10 mL). The reaction was heated to reflux and stirred overnight (115.75 hours). The ethanol was removed in vacuo, and the residue was dissolved in ethyl acetate, washed water and brine, dried over MgSO$_4$, and concentrated in vacuo to give a white solid which was passed through a column of silica gel with ethyl acetate/hexane (16%) and recrystallized from ethyl acetate/ isooctane to give the pyrazole as a white solid (0.32 g, mp 145.5°–50° C., 40% ). $^1$H NMR (CDCl$_3$) 300 MHz 7.90/d, J=8.9 Hz, 2H), 7.47 (d, J=8.7 Hz, 2H), 7.35 (d, J=8.5 Hz, 2H), 7.19 (d, J=8.5 Hz, 2H), 6.79 (s, 1 H), 5.18 (br s, 2H); $^{19}$F NMR (CDCl$_3$) 300 MHz: –84.66 (t), –113.70 (d).

EXAMPLE 13

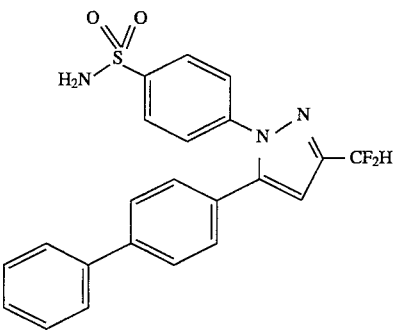

4-[5-(4-Biphenyl)-3-(difluoromethyl)-1H-pyrazol-1-yl]benzenesulfonamide

Step 1: Preparation of 4,4-difluoro-1-[4-biphenyl]-butane-1,3-dione)

Ethyl trifluoroacetate (2.08 g, 16.8 mmol) was placed in a 100 mL round bottom flask, and dissolved in ether (5 mL). To the stirred solution was added 25 weight sodium methoxide (3.73 g,17.2 mmol) followed by 4-acetylbiphenyl (2.97 g, 15.1 mmol), and THF (10 mL). The reaction was stirred at room temperature overnight (16.4 hours), treated with 3N HCl (8 mL), and extracted with ethyl acetate. The organic layer was collected and washed with brine, dried over HgSO$_4$, concentrated in vacuo, and recrystallized from methylene chloride/isooctane to give the diketone as a brown solid (3.24 g, mp 115°–18° C., 78%). $^1$H NMR (CDCl$_3$) 300 HHz 15.40 (br s, 1H), 8.01 (d, J=8.5 Hz, 2H), 7.74 (d, J=8.3 Hz, 2H), 7.63 {d, J=7.1 Hz, 2H), 7.49 (m, 3H), 6.61 (s, 1H), 6.02 (t, J=54.4 Hz,1H); $^{19}$F NMR (CDCl$_3$) 300 HHz: –126.91; M+274.

Step 2: Preparation of 4-[5-(4-biphenyl)-3- (difluoromethyl)-1H-pyrazol-1-yl]benzenesulfonamide The 4-sulfonamidophenyl hydrazine hydrochloride (0.40 g, 1.79 mmol) was added to a stirred solution of the diketone (0.44 g, 1.60 mmol) in ethanol (5 mL). The reaction was heated to reflux and stirred overnight (23.6 hours). The ethanol was removed in vacuo, and the residue was dissolved in ethyl acetate, washed with water (20 mL), washed with brine (20 mL), dried over MgSO$_4$, and concentrated in vacuo to give a brown solid which was recrystallized from ethyl acetate/isooctane to give the pyrazole as a brown solid (0.48 g, mp 167°–70° C., 70%) 1H NMR (CDCl$_3$) 300 MHz 7.91 (d, J=8.7 Hz, 2H), 7.59 (d, J=8.3 Hz, 4H), 7.26–7.51 (m, 7H), 6.79 (s and t, J=54.9 Hz 2 H), 4.89 (br s, 2H); $^{19}$F NMR (CDCl$_3$) 300 MHz: –112.72 (d); M+425.

EXAMPLE 14

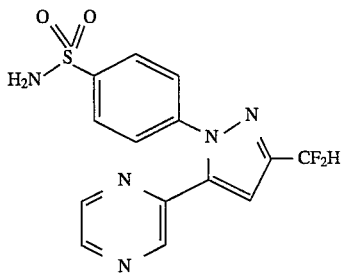

4-[5-(2-Pyrazinyl)-3-(difluoromethyl)-1H-pyrazol-1-yl]benzenesulfonamide

Step 1: Preparation of 4,4-difluoro-1-(2pyrazinyl)-butane-1,3-dione.

Ethyl difluoroacetane (2.23 g, 18 mmol) was placed in a 100 mL round bottom flask and dissolved in ether (10 mL). To the stirred solution was added 25 weight % sodium methoxide (4.68 g, 22 mmol) followed by acetylpyrazine (2.00 g,16 mmol). After two hours stirring at room temperature, a precipitate formed and THF (10 mL) was added to the reaction. The reaction was stirred an additional 25.9 hours, then treated with 3N HCl (10 mL). The organic layer was collected, washed with brine (20 mL), dried over $MgSO_4$, and concentrated in vacuo and recrystallized from methylene chloride/isooctane to give the diketone as a brown solid (2.23 g, mp 103°–110° C., 68%). $^1$H NMR (CDCl$_3$) 300 MHz 14.00 (br s, 1H), 9.31 (d, J=1.4 Hz, 1H), 8.76 (d, J=2.4 Hz, 1H), 8.68 (dd, J=1.4 Hz 2.4 Hz, 1H), 7.20 (s, 1H), 6.03 (t, J=54.0 Hz, 1H); $^{19}$F NMR (CDCl$_3$) 300 MHz: −127.16 (d); M+200.

Step 2: Preparation of 4-[5- (2 -pyrazinyl)-3-(di fluoromethyl)- 1H-pyrazol-1-yl]benzenesulfonamide The 4-sulfonamidophenyl hydrazine hydrochloride (0.37 g, 1.65 mmol) was added to a stirred suspension of the diketone (0.30 g, 1.50 mmol) in ethanol (10 mL). The reaction was heated to reflux and stirred for 5.3 hours. The ethanol was removed in vacuo, and the residue was dissolved in ethyl acetate, washed with water (20 mL), brine (20 mL), dried over $MgSO_4$, and concentrated in vacuo to give a brown solid (0.36 g) which was recrystallized from ethyl acetate/ethanol/isooctane to give the pyrazole as a brown solid (0.20 g, mp 191°–94° C., 38% $^1$H NMR (acetone d$^6$) 300 MHz 8.94(d, J=1.4 Hz, 1H), 8.62 (d, J=2.4 Hz, 1H), 8.52 (dd, j=1.4 Hz 2.4 Hz, 1H): 7.95 (d, J=8.7 Hz, 2H), 7.61 (d, J=8.7 Hz, 2H), 7.30 (s, 1H), 7.02 (t, J=54.6 Hz, 1H), 6.73 (br s, 2 H); $^{19}$F NMR (acetone d$^6$) 300 MHz: −113.67 (d) ; M+351.

EXAMPLE 15

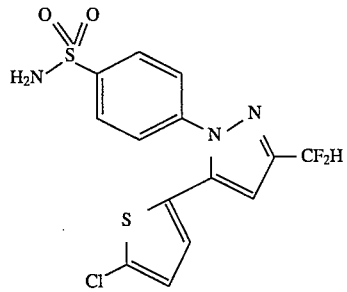

4-[5-(5-Chloro-2-thienyl)-3-(difluoromethyl)-1H-pyrazol-1-yl]benzenesulfonamide

Step 1: Preparation of 4,4-difluoro-1-[5-chloro-2-thienyl]-butane-1,3-dione

Ethyl difluoroacetate (3.51 g, 28.3 mmol) was placed in a 100 mL round bottom flask and dissolved in ether (10 mL). To the stirred solution was added 25 weight % sodium methoxide (6.12 g, 28.3 mmol) followed by 2-acetyl-5-chlorothiophene (4.12 g, 25.6 mmol). A pink precipitate formed after 5 minutes which was dissolved by adding ether (10 mL) and THF (10 mL) to the reaction. The reaction was stirred at room temperature overnight (15.75 hours), then treated with in HCl (15 mL). The organic layer was collected and washed with brine (20 mL), dried over $MgSO_4$, and concentrated in vacuo to give a red solid (5.94 g) which was recrystallized from methylene chloride/isooctane to give the diketone as a yellow solid (2.02 g, mp 72°–77° C., 33%). $^1$H NMR (CDCl$_3$) 300 MHz 14.60 (br s, 1H), 7.57 (d, J=4.2 Hz, 1H), 7.01 (d, J=4.2 Hz, 1H), 6.32 (s, 1H), 6.04 (t, J=54.2 Hz, 1H); $^{19}$F NMR (CDCl$_3$) 300 MHz: −127.01 (d); M+238.

Step 2; Preparation of 4-[5-(5-chloro-2-thienyl)-3- (difluoromethyl)-1H-pyrazol-1-yl]benzenesulfonamide.

The 4-sulfonamidophenyl hydrazine hydrochloride (0.31 g, 1.39 mmol) was added to a stirred solution of the diketone (0.30 g, 1.26 mmol) in ethanol (10 mL). The reaction was heated to reflux and stirred 5.5 hours. The ethanol was removed in vacuo, and the residue was dissolved in ethyl acetate, washed with water (20 mL), washed with brine (20 mL), dried over $MgSO_4$, and concentrated in vacuo to give a yellow solid (0.55 g) which was recrystallized from ethyl acetate/isooctane to give the pyrazole as a white solid (0.38 g, mp 168°–70° C., 78 %). $^1$H NMR (acetone d$^6$) 300 MHz 8.03 (d, J=8.7 Hz, 2H), 7.70 (d, J=8.7 Hz, 2H), 7.04 (m, 4H), 6.76 (br s, 2 H) ; $^{19}$F NMR (acetone d$^6$) 300 MHz: −113.71 (d) ; $^{13}$C NMR (acetone d$^6$) 300 MHz 148.01(t), 144.69, 141.64, 137.70, 131.59, 128.90, 128.53,127.48, 127.40 , 126.47, 111.36(t), 105.89(t); M+389/391.

EXAMPLE 16

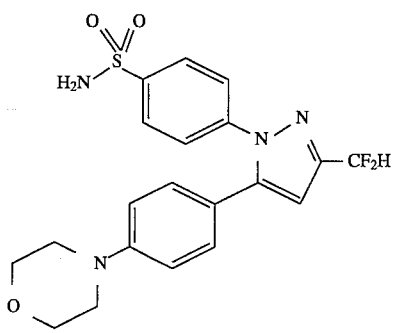

4-[5-(4-(Morpholino)phenyl)-3-(difluoromethyl)-1H-pyrazol-1-yl]benzenesulfonamide Step. 1: Preparation of 4,4-difluoro-1-[4-(morpholino)phenyl]butane-1,3-dione Ethyl difluoroacetate (2.30 g, 18.5 mmol) was placed in a 100 mL round bottom flask and dissolved in THF (25 mL). To the stirred solution was added 25 weight % sodium methoxide (4.90 g, 22.6 mmol) followed by 4'-morpholinoacetophenone (3.45 g, 16.8 mmol). The reaction was stirred at room temperature overnight (15.8 hours), then treated with 3N HCl (13 mL). The reaction was extracted with ethyl acetate (20 mL), washed with brine (20 mL), dried over MgSO$_4$, and concentrated in vacuo give a green solid (4.36 g) which was recrystallized from methylene chloride/isooctane to give the diketone as a yellow solid (3.27 g, mp 102°–3° C., 69%). $^1$H NMR (CDCl$_3$) 300 MHz 15.80 (br s, 1H), 7.86 (d, J=9.1 Hz, 2H), 6.90 (d, J=9.1 Hz, 2H), 6.46 (s, 1H), 5.99 (t, J=54.4 Hz, 1H), 3.84 (m, 4 H), 3.36 (m, 4H); $^{19}$F NMR (CDCl$_3$) 300 MHz: −126.75 (d); M+283.

Step 2: Preparation of 4-[5-(4-(morpholino)phenyl)-3-(difluoromethyl)-1H-pyrazol-1-yl]benzenesulfonamide The 4-sulfonamidophenyl hydrazine hydrochloride (0.20 g, 0.89 mmol) was added to a boiling solution of the diketone (0.23 g, 0.81 mmol) in ethanol (5 mL). The reaction was stirred 5.0 hours. The ethanol was removed in vacuo, and the residue was dissolved in ethyl acetate, washed with water 20 mL), washed with brine (20 mL), dried over MgSO$_4$, and concentrated in vacuo to give a yellow foam (0.36 g) which was recrystallized from methylene chloride/isooctane to give the pyrazole as a yellow solid (0.25 g, mp 167°–71° C., 71%). $^1$H NMR (CDCl$_3$) 300 MHz 7.88 (d, J=8.7 Hz, 2H), 7.49 (d, J=8.9 Hz, 2H), 7.10 (d, J=8.9 Hz, 2 H), 6.86 (d, J=9.1Hz, 2 H), 6.75 (t, J=55.0 Hz, 1H), 6,67 (s, 1H) 4.91 (br s, 2 H}, 3.86 (m, 4 H), 3.21 (m, 4H); $^{19}$F NMR (CDCl$_3$) 300 MHz: −112.67 (d); M+434.

EXAMPLE 17

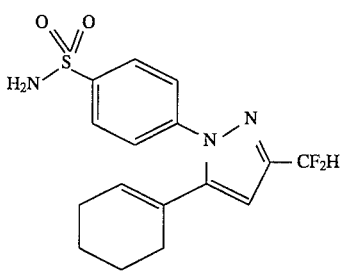

4-[5-(1-Cyclohexenyl)-3-(difluoromethyl)-1H-pyrazol-1-yl]benzenesulfonamide

Step 1: Preparation of 4,4 -difluoro-1-[2-cyclohexenyl]-butane-1,3-dione

Ethyl difluoroacetate (4.71 g, 38 mmol) was placed in a 100 mL round bottom flask and dissolved in ether (20 mL). To the stirred solution was added 25 weight % sodium methoxide (9.68 g, 45 mmol) followed by 1-acetyl-1-cyclohexene (4.27 g, 34 mmol). The reaction was stirred at room temperature overnight (17.5 hours), then treated with 3N HCl (20 mL). The organic layer was collected and washed with brine (20 mL), dried over HgSO$_4$, and concentrated in vacuo to give a brown oil (6.48 g, 93%). $^1$H NHR (CDCl$_3$, 300 MHz 15.00 (br s, 1H) 6.09 (s,1H), 5.92 (t, J=54.4 Hz,1H), 2.31 (m, 4H), 1.64 (m, 4H); $^{19}$F NMR (CDCl$_3$) 300 HHz: −126.94; H+202.

Step 2: Preparation of 4-[5-(1-cyctohexenyl)-3- (difluoromethyl)-1H-pyrazol-1-yl]benzenesulfonamide The 4-sulfonamidophenyl hydrazine hydrochloride (0.71 g, 3.17 mmol) was added to a stirred solution of the diketone 0.58 g, 2.87 mmol) in ethanol (5 mL). The reaction was heated to reflux and stirred overnight (14.6 hours). The ethanol was removed in vacuo, and the residue was dissolved in ethyl acetate, washed with water (35 mL), washed with brine (35 mL), dried over MgSO$_4$, and concentrated in vacuo to give a brown oil which was passed through a column of silica gel with 16% ethyl acetate/hexane to isolate the pyrazole as a white solid (0.41 g, mp 160°–61° C., 40%) $^1$H NMR (CDCl$_3$) 300 MHz 7.96 (d, J=8.5 Hz, 2H), 7.67 (d, J=8.6 Hz, 2H), 6.70 (t, J=55.0 Hz 1 H), 6.50 (s, 1H), 5.90 (br s, 1H), 5.22 (br s, 2H), 2.02–2.11(m, 4H), 1.70–1.61 (m, 4H); $^{19}$F NMR (CDCl$_3$) 300 MHz: −112.69 (d); M+353.

EXAMPLE 18

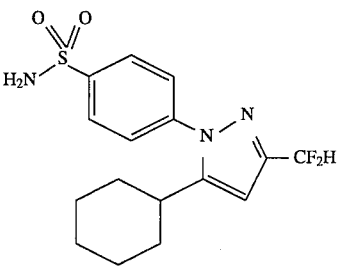

4-[5-(1-Cyclohexyl)-3-(difluoromethyl)-1H-pyrazol-1-yl]benzenesulfonamide

The 4- [5- (1-cyclohexyl)-3-(difluoromethyl)-1H-pyrazol-1-yl]benzenesulfonamide (0.31 g, 0.88 mmol) was dissolved in ethanol (15 mL), 10% palladium on charcoal was added, and the suspension was stirred at room temperature under hydrogen (36 psi) for 18.25 hours. The reaction was filtered through celite, and the ethanol removed in vacuo to give a white solid, which was recrystallized from methylene chloride/isooctane (0.31 g, mp 199°–203° C., 99%). $^1$H NMR (acetone d$^6$) 300 MHz 8.05 (d, J=8.7 Hz, 2H), 7.60 (d, J=8.5 Hz, 2H), 6.69 (t, J=55.0 Hz 1 H), 6.47 (s, 1H), 5.02 (br s, 2H), 2.67 (m, 1H), 1.71–1.88 (m, 5H), 1.24–1.43 (m, 5H); $^{19}$F NMR (acetone d$^6$) 300 MHz: −112.86 (d).

EXAMPLE 19

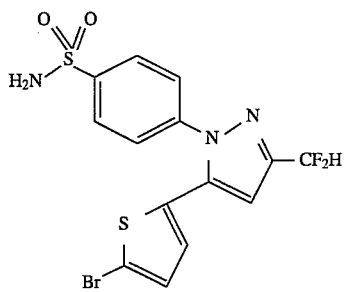

4-[5-(5-Bromo-2-thienyl)-3-(difluoromethyl)-1H-pyrazol-1-yl]benzenesulfonamide

Step 1. Preparation of 4,4-difluoro-1-[5-bromo-2-thienyl]-butane-1,3-dione

Ethyl difluoroacetane (2.43 g, 19.6 mmol) was placed in a 100 mL round bottom flask, and dissolved in ether (15 mL). To the stirred solution was added 25 weight % sodium methoxide (4.23 g, 19.5 mmol) followed by 2-acetyl-5-bromothiophene (3.59 g, 17.5 mmol). After hours a precipitate formed and THF 15 mL was added to allow stirring to continue. The reaction was stirred at room temperature 6.2 hours, then treated with 3N HCl (20 mL). The organic layer was collected and washed with brine, dried over MgSO$_4$, and concentrated in vacuo to give a yellow oil which was crystallized from methylene chloride/isooctane to give yellow needles. (3.63 g, mp 83.5°–85° C., 73%). $^1$H NMR (CDCl$_3$) 300 MHz 14.60 (br s, 1H), 7.53 (d, J=4.0 Hz, 1H), 7.15 (d, J=4.0 Hz, 1H), 7.19 (m, 1H) 6 32 (s, 1H) 6 04 (t, J=54.2 Hz, 1H); $^{19}$F NMR (CDCl$_3$) 300 MHz: −127.00 (d); M+282.

Step 2. Preparation of 4-[5-(5-bromo-2-thienyl)-3-( difluoromethyl)-1H-pyrazol-1-yl]benzenesulfonamide The 4-sulfonamidophenyl hydrazine hydrochloride (0.42 g, 1.88 mmol) was added to a stirred solution of the diketone (0.48 g, 1.70 mmol) in ethanol (5 mL). The reaction was healed to reflux and stirred overnight (17.25 hours). The ethanol was removed in vacuo, and the residue was dissolved in ethyl acetate, washed with water (20 mL), washed with brine (20 mL), dried over MgSO$_4$, and concentrated in vacuo to give a while solid (0.67 g) which was recrystallized from ethyl acetate/isooctane to give the pyrazole as a while solid (0.39 g, mp 168°–69° C., 53%). $^1$H NMR (acetone d$^6$) 300 MHz 8.03 (d, J=8.5 Hz, 2H), 7.70 (d, J=8.7Hz, 2H), 7.16 (d and part of CF$_2$H triplet, J=4.0 Hz 1.25 H) , 6.97 (m and part of CF$_2$H triplet, 2.5 H) 6.78 (br s and part of CF$_2$H triplet, 2.25 H); $^{19}$F NMR (acetone d$^6$) 300 MHz: −113.70 (d); M+Li 440/442.

EXAMPLE 20

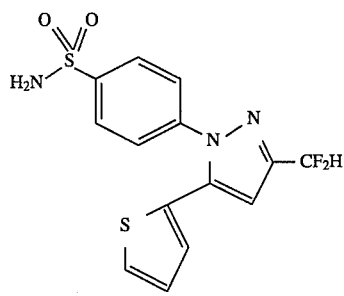

4-[5-(2-Thienyl)-3-(difluoromethyl)-1H-pyrazol-1-yl]benzenesulfonamide

Step 1: Preparation of 4,4-difluoro-1-[2-thienyl]-butane-1,3-dione

Ethyl difluoroacetate (1.84 g,14.8 mmol) was placed in a 100 mL round bottom flask and dissolved in ether (5 mL). To the stirred solution was added 25 weight % sodium methoxide (3.39 g, 15.7 mmol) followed by 2-acetylthiophene (1.72 g,13.6 mmol). The reaction was stirred at room temperature overnight (15.67 hours), then treated with 3N HCl (8 mL). The organic layer was collected and washed with brine, dried over MgSO$_4$, concentrated in vacuo, and recrystallized from methylene chloride/isooctane to give a brown solid (1.38 g, mp 78°–80° C., 50%) $^1$H NMR (CDCl$_3$) 300 MHz 14.90 (br s, 1H), 7.80 (d, J=4.0 Hz, 1H), 7.71 (d, J=3.8 Hz, 1H), 7.19 (m, 1H), 6.41 (s, 1H), 6.04 (t, J=54.2 Hz, 1H); $^{19}$F NMR CDCl$_3$ ) 300 MHz: −126.98 (d); M+204.

Step 2: Preparation of 4-[5-(2-thienyl)-3-(difluoromethyl)-1H-pyrazol-1-yl]benzenesulfonamide The 4-sulfonamidophenyl hydrazine hydrochloride 0.43 g, 1.92 mmol) was added to a stirred solution of the diketone ( 0.36 g, 1.76 mmol) in ethanol (5 mL). The reaction was heated to reflux and stirred overnight (17.67 hours). The ethanol was removed in vacuo, and the residue was dissolved in ethyl acetate, washed with water (20 mL), washed with brine (20 mL), dried over MgSO$_4$, and concentrated in vacuo to give a brown solid which was recrystallized from ethyl acetate/isooctane to give the pyrazole as brown needles (0.30 g, mp 190°–91° C., 48%). $^1$H NMR (acetone d$^6$) 300 MHz 8.00 (d, J=8.2 Hz, 2H), 7.62 (m, 3H), 7.11 (m, and part of CF2H triplet, 2.25 H), 6.93 (s and part of CF$_2$H triplet, 1.5 H) 6.76 (br s and part of CF$_2$H triplet, 2.25 H); $^{19}$F NMR (acetone d$^6$) 300 HHz: −113.60 (d); $^{13}$C NMR (acetone d$^6$) 300 MHz 146.96(t), 144.43,141.98, 138.84, 129.53,129.02, 128.38, 127.86, 127.26,126.36, 114.46(t), 105.57(t); M+Li 367.

EXAMPLE 21

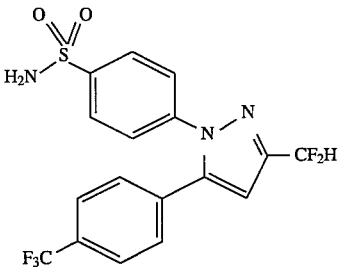

4-[5-(4-[Trifluoromethyl]phenyl)-3-(difluoromethyl)-1H-pyrazol-1-yl]benzenesulfonamide Step 1: Preparation of 4,4-difluoro-1-[4-(trifluoromethyl)phenyl]-butane-1,3-dione Ethyl difluoroacetate (2.78 g, 22.4 mmol) was placed in a 100 mL round bottom flask and dissolved in ether (10 mL). To the stirred solution was added 25 weight % sodium methoxide (6.02 g, 27.8 mmol) followed by 4'-(trifluoromethyl)acetophenone (3.80 g, 20.2 mmol) and THF (20 mL). The reaction was stirred at room temperature overnight (15.6 hours), then treated with 3N HCl (20 mL). The organic layer was collected and washed with brine, dried over MgSO$_4$, concentrated in vacuo to give a brown oil (4.88 g, 91%). $^1$H NMR (acetone d$^6$) 300 MHz 15.10 (br s, 1H), 8.03 (d, J=8.7 Hz, 2H), 7.77 (d, J=8.5 Hz, 2H), 6.59 (s, 1H), 6.02 (t, J=54.2 Hz, 1H); $^{19}$F NMR (acetone d$^6$) 300 MHz: −63.70 (s), −127.10 (d); M+266.

Step 2; Preparation of 4-[5-(4-[trifloromethyl]phenyl)-3-(difluoromethyl)-1H-pyrazol-1-yl]benzenesulfonamide The diketone (0.41g, 1.54 mmol) was added to a stirred suspension of 4-sulfonamidophenyl hydrazine hydrochloride (0.39 g, 1.74 mmol) in ethanol (5 mL). The reaction was heated to reflux and stirred overnight (17.4 hours). The ethanol was removed in vacuo., and the residue was dissolved in ethyl acetate, washed with water (20 mL), washed with brine 20 mL), dried over HgSO$_4$, and concentrated in vacuo to give a brown solid which was recrystallized from ethyl acetate/isooctane to give the pyrazole as a tan solid (0.30 g, mp 202°–5° C., 46%). $^1$H NMR (acetone d$^6$) 300 MHz 7.95 (d, J=8.9 Hz, 2H), 7.76 (d, J=8.2 Hz, 2H), 7.62 (d, J=8.1 Hz, 2H), 7.58 (d, J=8.7 Hz, 2H), 7.03 (s, 1H), 6.99 (t, J=54.6 Hz, 1H), 6.73 (br s, 2H); $^{19}$F NMR (acetone d$^6$) 300 MHz: −63.69 (s), −113.57 (d); H+H 418.

EXAMPLE 22

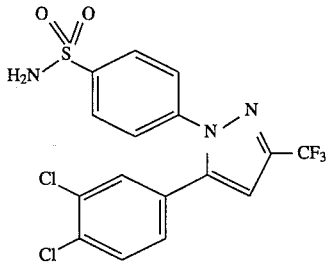

4-[5-(3,4-Dichlorophenyl)-3-(trifluoromethyl)-1H-pyrazol-1-yl]benzenesulfonamide 3,4-Dichloroacetophenone (6.24 g, 33 mmol) was dissolved in 25 mL methanol and 25% NaOMe in methanol (9 mL, 39.4 mmol) was added. The mixture was stirred at 25° C. for 5 minutes and ethyl trifluoroacetate (5 mL, 42 mmol) was added. The mixture was heated at 60° C. for 24 hours, cooled and the volume reduced by 50%. The mixture was poured into 100 mL of 10% HCl and extracted with four 75 mL portions of ethyl acetate. The combined extracts were dried over Na$_2$SO$_4$, filtered and concentrated in vacuo to afford the crude diketone as a brown gum (8.54 g, 30 mmol) which was used without further purification. The crude diketone (3.16 g, 11.1 mmol) and 4-sulfonamidophenylhydrazine.HCl (3.31 g, 14.8 mmol) were dissolved in 75 mL of absolute ethanol and the mixture stirred at reflux for 24 hours. The mixture was cooled, filtered and concentrated in vacuo to afford the crude pyrazole. Recrystallization from diethyl ether/hexane afforded the pure pyrazole (2.43 g, 51%) as a yellow solid, mp 145°–147° C.; Anal. calc'd for C$_{16}$H$_{10}$N$_3$O$_2$SCl$_2$F$_3$: C, 44.05; H, 2.31; N, 9.63; Cl, 16.25. Found: C, 44.00; H, 2.20; N, 9.63; Cl, 16.46.

EXAMPLE 23

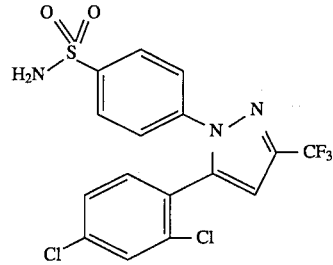

4-[5-(2,4-Dichlorophenyl)-3-(trifluoromethyl)-1H-pyrazol-1-yl]benzenesulfonamide Following the procedure of Example 22, but substituting 2,4-dichloroacetophenone for 3,4-dichloroacetophenone afforded 4-[5-(2,4-dichlorophenyl)-3-(trifluoromethyl)-1H-pyrazol-1-yl]benzenesulfonamide as a tan solid, mp 153°–155° C.; Anal. calc'd for C$_{16}$H$_{10}$N$_3$O$_2$SCl$_2$F$_3$–0.10 H$_2$O: C, 43.87; H, 2.35; N, 9.59. Found: C, 43.78; H, 2.13; N, 9.56.

EXAMPLE 24

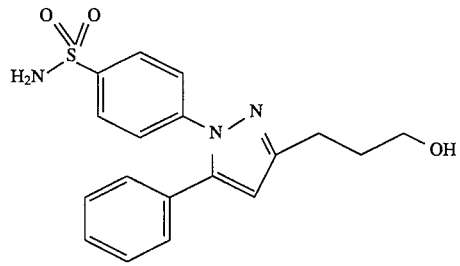

4-[5-Phenyl-3-(3-hydroxylpropyl)-1H-pyrazol-1-yl]benzenesulfonamide

A 60% dispersion of sodium hydride in mineral oil (4.0 g, 100 mmol) was twice washed with hexane (100 mL each) and dried under a stream of nitrogen. Ether (300 mL) was added followed by dropwise addition of ethanol (0.25 mL) and γ-butyrolactone (4.0 mL, 52 mmol). The mixture was cooled to 10° C. and acetophenone (5.8 mL, 50 mmol) in ether (40 mL) was added dropwise over 1 hour. The mixture was warmed to 25° C. and stirred overnight. The mixture was cooled to 0° C. and quenched with ethanol (5 mL) followed by 10% aqueous ammonium sulfate (100 mL). The organic solution was separated, dried over Na$_2$SO$_4$ and concentrated. The residue was chromatographed on silica gel with 1:1 hexane/ethyl acetate to give the desired diketone (3.4 g) as an oil. Pyridine (0.34 mL, 4.2 mmol) and the diketone (700 mg, 3.4 mmol) in methanol (3 mL) were added to a slurry of 4-sulfonamidophenylhydrazine-HCl (750 mg, 3.4 mmol) in methanol (8 mL). The mixture was stirred at 25° C. overnight and concentrated in vacuo. The residue was dissolved in methylene chloride and the solution washed with 1N HCl. The organic solution was separated, dried and concentrated. The residue was chromatographed on silica gel using ethyl acetate to give the desired pyrazole (435 mg) as a solid: Anal. calc'd for $C_{18}H_{19}N_3O_3S$: C, 60.49; H, 5.36; N, 11.75. Found: C, 60.22; H, 5.63; N, 11.54.

EXAMPLE 25

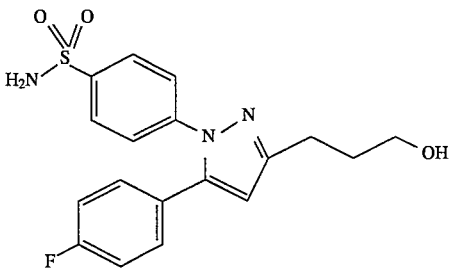

4-[5-(4-Fluorophenyl)-3-(3-hydroxypropyl)-1H-pyrazol-1-yl]benzenesulfonamide

Following the procedure of Example 24, but substituting 4-fluoroacetophenone for acetophenone afforded 4-[5-(4-fluorophenyl)-3-(3-hydroxypropyl)-1H-pyrazol-1-yl]benzenesulfonamide. Anal. calc'd for $C_{18}H_{18}N_3O_3SF–0.25\ H_2O$: C, 56.90; H, 4.91; N, 11.05. Found: C, 56.80; H, 4.67; N, 11.02.

EXAMPLE 26

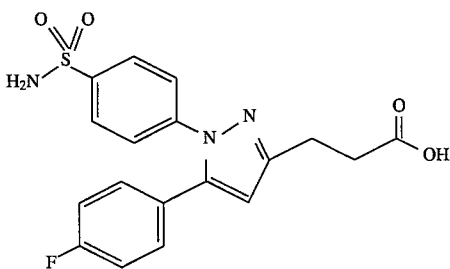

4-[4-(Aminosulfonyl)phenyl]-5-(4-fluorophenyl)-1H-pyrazole]-3-propanoic acid

Jones reagent (0.64 mL of a 2.67M solution) was added dropwise to a solution of 4-[5-(4-fluorophenyl)-3-(3-hydroxypropyl)-1H-pyrazol-1-yl] benzenesulfonamide from Example 25 (295 mg, 0.78 mmol) in acetone (8 mL). The mixture was stirred at 25° C. for 2 hours. The solution was filtered and the filtrate concentrated in vacuo. The residue was dissolved in ethyl acetate and washed with water (3X). The organic solution was dried over $MgSO_4$ and concentrated. The residual oil was crystallized from ether/hexane to give the desired acid. (149 mg, mp 180°–182° C.) Anal. calc'd for $C_{18}H_{16}N_3O_4SF$: C, 55.52; H, 4.14; N, 10.79. Found: C, 55.47; H, 4.22; N, 10.50.

EXAMPLE 27

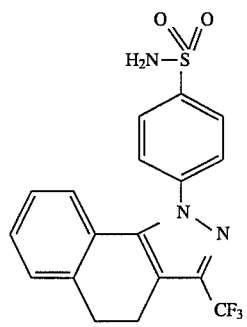

4,5-Dihydro-4-[3-trifluoromethyl]-1H-benz[g]indazol-1-yl]benzenesulfonamide

Step 1: Preparation of 2-trifluoroacetyl-1-tetralone

A 250 mL one necked round bottomed flask equipped with a reflux condenser, nitrogen inlet and provisions for magnetic stirring was charged with ethyl trifluoroacetate (28.4 g, 0.2 mol) and 75 mL of ether. To this solution was added 48 mL of 25% sodium methoxide in methanol (0.21 mol). A solution of 1-tetralone (29.2 g, 0.2 mol) in 50 mL of ether was then added over about 5 min. The reaction mixture was then stirred at room temperature for 14 h and then was diluted with 100 mL of 3N HCl. The phases were separated and the organic layer washed with 3N HCl, brine, dried over anhyd. $MgSO_4$, filtered and concentrated in vacuo. The residue was then taken up in 70 mL of boiling ethanol/water and allowed to cool to room temperature whereupon crystals of 2-trifluoroacetyl-1-tetralone formed which were isolated by filtration and air dried to give 32 g, 81% of pure product with mp 48°–49° C. $^1H$ NMR $CDCl_3 \delta 2.8$ (m, 2H), 2.9 (m, 2H), 7.2 (d, g=3.0 Hz, 1H), 7.36 {m, 1H, 7.50 (m, 1H), 7.98 (m, 1H); $^{19}F$ NMR $CDCl_3 \delta$ –72.0. EI GC-MS M+=242.

Step 2: Preparation of 4,5-dihydro-4-[3-(trifluoromethyl)-1H-benz[g]indazol-1-yl]benzenesulfonamide A 100 mL one necked round bottomed flask equipped with reflux condenser, nitrogen inlet and provisions for magnetic stirring was charged with 2-trifluoroacetyl-1-tetralone (1.21 g, 5.0 mmol), 4-sulfonamido phenylhydrazine hydrochloride (1.12 g, 5.0 mmol) and 25 mL of absolute ethanol. The solution was then warmed to reflux for 15 h and then concentrated in vacuo. The residue was dissolved in ethyl acetate and then washed with water, brine, dried over anhyd. $MgSO_4$, filtered and concentrated in vacuo. The residue was recrystallized from a mixture of ethyl acetate and isooctane to give g, 71% of pure product with mp 257°–258° C. $^1H$ NMR ($CDCl_3/CD_3OD$, 4:1) $\delta$ 2.7 (m, 2H), 2.9 (m, 2H), 6.6 (m, 1H), 6.9 (m, 1H), 7.1 (m, 1H), 7.16 (m, 1H), 7.53 (m, 2H), 7.92 (m, 2H); $^{19}F$ NMR $CDCl_3 \delta$ –62.5. FAB-MS M+H=394.

EXAMPLE 28

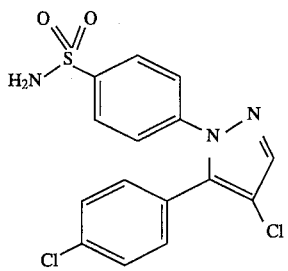

4-[5-(4-Chlorophenyl)-4-chloro-1H-pyrazol-1-yl]
benzenesulfonamide

Step 1. Preparation of 3-(4-Chlorophenyl)-3-ketopropionaldehyde

A 4-necked round-bottomed flask equipped with mechanical stirrer, nitrogen inlet, reflux condenser, constant pressure addition funnel and thermometer was charged with 4-chloroacetophenone (77.0 g, 0.5 mol), ethyl formate (40.8 g, 0.55 mol) and 800 mL of ether. The stirrer was started and the solution treated with a solution of 25% sodium methoxide in methanol (123 g, 0.55 mol) from the addition funnel over about 0.5 hour. A heavy white precipitate formed as the sodium methoxide was added. The reaction was stirred at room temperature for 5 hours and was then diluted with an additional 800 mL of ether, the precipitate was isolated on a Buchner funnel and washed with thouroughly with ether. The precipitate was dried in vacuo and then placed in a large Erlenmeyer flask and acidified with 3N HCl and then extracted with ethyl acetate. The ethyl acetate solution was washed with brine, dried over anhydrous $MgSO_4$, filtered and concentrated in vacuo to give a thick orange oil, 60.9 g, 67% of 3-(4-chlorophenyl)-3-ketopropionaldehyde, IR (neat) 1585 $cm^{-1}$.

Step 2 Preparation of 4-[5-f4-chlorophenyl)-1H-pyrazol-1-yl]benzenesulfonamide

A 250 mL one-necked round-bottomed flask equipped with reflux condenser, nitrogen inlet and provisions for magnetic stirring was charged with 3-(4-chlorophenyl)-3-ketopropionaldehyde (18.3 g, 0.1 mol), 4-sulfonamidophenylhydrazine hydrochloride (11.2 g, 0.05 mol) and 100 mL of absolute ethanol. The solution was heated to reflux for 15 hour and then diluted with 100 mL of water and allowed to stand whereupon a white solid formed that was isolated by filtration on a Buchner funnel and air dried to provide 12.6 g, 76% of 4-[5-(4-chlorophenyl)-1H-pyrazol-1-yl] benzenesulfonamide, mp 185°–187° C. $^1H$ nmr ($CDCl_3$/300MHz) 7.89(d, J=8.7Hz, 2H), 7.76 (d, J=1.8Hz, 1H), 7.43 (d, J=8.7Hz, 2H), 7.34 (d, J=8.7Hz, 2H), 7.17(d, J=8.7Hz, 2H), 6.53(d, J=1.8Hz, 1H), 4.93 (brs, 2H), mass spectrum MH+= 334.

Step 3. Preparation of 4-[5-(4-chlorophenyl)-4-chloro-1H-pyrazol-1-yl]benzenesulfonamide A 100 mL three-necked round-bottomed flask equipped with reflux condenser, gas dispersion tube and provisions for magnetic stirring was charged with 4-[5-(4-chlorophenyl)-1H-pyrazol-1-yl] benzenesulfonamide (500 mg, 1.2 mmol) and 50 mL of glacial acetic acid. The solution was stirred at room temperature and treated with a stream of chlorine gas for a period of 15 minutes. The solution was then stirred at room temperature for 1.25 hours and then diluted with 100 mL of water. The solution was then extracted three times with ether and the combined ethereal phase washed with brine, dried over anhyd. $MgSO_4$, filtered, and concentrated in vacuo to give a white solid that was recrystallized from ether/petroleum ether to provide 400 mg, 75% of 4-[5-(4-chlorophenyl)-4-chloro-1H-pyrazol-1 -yl]benzenesulfonamide, $^1H$ nmr $CDCl_3$/300MHz) 8.06 (s, 1H), 7.81(d, J=8.4Hz, 2H), 7.53(d, J=8.4Hz 2H), 7.43 (brs, 2H), 7.42 (d, J=8.4Hz, 2H), 7.32(d, J=8.4Hz, 2H).

EXAMPLE 29

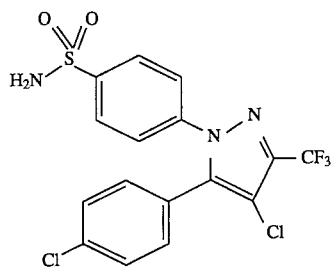

4-[5-(4-Chlorophenyl)-3-(trifluoromethyl)-4-chloro-1H-pyrazol-1-yl]benzenesulfonamide A 100 mL three-necked round-bottomed flask equipped with reflux condenser, gas dispersion tube and provisions for magnetic stirring was charged with 4-[5-(4-chlorophenyl)-3-trifluoromethyl-1H-pyrazol-1- yl]benzenesulfonamide (500 mg, 1.2 mmol) and 50 mL of glacial acetic acid. The solution was stirred at room temperature and treated with a stream of chlorine gas for a period of 15 minutes. The solution was then stirred at room temperature for 1.25 hours and then diluted with 100 mL of water. The solution was then extracted three times with ether and the combined ethereal phase washed with brine, dried over anhyd. $MgSO_4$, filtered, and concentrated in vacuo to give a white solid that was recrystallized from ether/petroleum ether to provide 390 mg, 75% of 4-[5-(4-chlorophenyl)-4-chloro-3-trifluoromethyl-1H-pyrazol-1-yl] benzenesulfonamide mp 180°–182 ° C. $^1H$ nmr ($CDCl_3$/300MHz) 7.97(d, J=6.6Hz, 2H), 7.49 (d, J=6.3Hz, 2H), 7.45 (d, J=6.3Hz, 2H), 7.25 (d, J=6.6Hz, 2H), 5.78(brs, 2H).

EXAMPLE 30

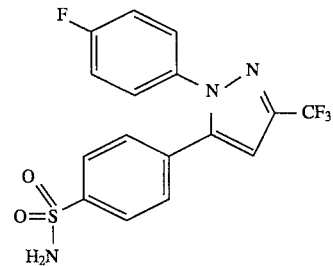

4-[1-(4-Fluorophenyl)-3-(trifluoromethyl)1H-pyrazol-5-yl]benzenesulfonamide

Step 1: Preparation of N,N-bis(4-methoxybenzyl)-4-(aminosulfonyl)acetophenone

To a solution of 4-(aminosulfonyl)acetophenone (2.0 g, 9.0 mmol) in dimethylsulfoxide (25 mL) was added NaOH (450 mg, 19.0 mmol). The reaction mixture was stirred for 45 minutes and then 4-methoxybenzyl bromide (3.5 g, 19.0 mmol) in dimethylsulfoxide (5 mL) was added via canula. The mixture was stirred at room temperature for 24 hours and partitioned between ethyl acetate and pH 7 buffer. The aqueous solution was extracted with ethyl acetate. The organic solution was dried (MgSO$_4$) and concentrated. The residue was chromatographed on silica (2:1 hexane:ethyl acetate) to give the desired product (815 mg, 21%).

Step 2: Preparation of N,N-bis(4-methoxybenzyl)-4-[1-(4-fluorophenyl)-3trifluoromethyl-1H-pyrazol-5-yl]benzenesulfonamide Ethyl trifluoroacetate was placed in a 500 mL three-necked round bottom flask, and dissolved in methyl tert-butyl ether (75 mL). To the stirred solution was added 25 weight % sodium methoxide via an addition funnel over a 2 minute period. Next the protected acetophenone from step 1 was dissolved in methyl tert-butyl ether (20 mL), and added no the reaction dropwise over 5 minutes. After stirring overnight (15.75 hours), 3N HCl (70 mL) was added. The organic layer was collected, washed with brine (75 mL), dried over MgSO$_4$, filtered, and concentrated in vacuo. The solid was recrystallized from iso-octane to give the dione. 4-Flourophenyl hydrazine hydrochloride was added to a stirred solution of the dione in ethanol (50 mL). The reaction was heated to reflux and stirred for 20 hours. After cooling to room temperature, the reaction mixture was concentrated in vacuo. The residue was taken up in ethyl acetate and washed with water and brine and dried over MgSO$_4$, filtered, and concentrated in vacuo to give a light brown solid which was recrystallized from ethyl acetate and iso-octane to give the protected pyrazole.

Step 3: Preparation of 4-[1-(4-fluorophenyl)-3-trifluoromethyl-1H-pyrazol-5-yl] benzenesulfonamide To a solution of the protected pyrazole (50 mg, 0.08 mmol) in acetonitrile (1 mL) and water (0.3 mL) was added ceric ammonium nitrate (360 mg, 0.65 mmol). The reaction solution was kept am room temperature for 16 hours. The solution was poured into water (15 mL) and extracted with ethyl acetate (2×25 mL). The combined extracts were dried (MgSO$_4$) and concentrated. The residue was chromatographed on silica (2:1 hexane:ethyl acetate) to give the desired product (13 mg, 42%). $^1$H NMR (CD$_3$OD) 7.88 (d,2H), 7.46 (d, 2H), 7.39 (dd, 2H), 7.21 (t, 2H), 7.06 (s, 1H).

BIOLOGICAL EVALUATION

Rat Carrageenan Foot Pad Edema Test

The carrageenan foot edema test was performed with materials, reagents and procedures essentially as described by Winter, et al., (*Proc. Soc. Exp, Biol. Med.*, 111, 544 (1962)). Male Sprague-pawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Ottertess and Bliven, *Laboratory Models for Testing NSAIDs*, in *Non-steroidal Anti-Inflammatory Drugs*, (J. Lombardino, ed. 1985)). Results are shown in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-pawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 20 mg/kg body weight |
| --- | --- | --- |
| 1 | 44 | 51 |
| 1f | 42* | |
| 2 | 39 | 46 |

*Assay performed at 20 mg/kg body weight

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutisal composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stoatic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parentoral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

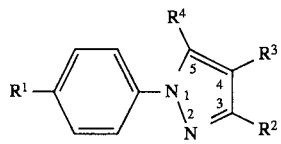

wherein $R^1$ is sulfamyl;

wherein $R^2$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylalmido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl and heterocyclic;

wherein $R^3$ is selected from hydrido, alkyl, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamicio, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, dialkylsulfamyl, N-alkyl-N-arylsulfamyl, heterocyclic, heterocycloalkyl and aralkyl; and wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N, N-dialkylamino, heterocyclic, nitro and acylamino;

provided $R^2$ and $R^3$ are not identical radicals selected from hydrido, carboxyl and ethoxycarbonyl; further provided that $R^2$ is not carboxyl when $R^3$ is hydrido and when $R^4$ is phenyl; and further provided that $R^3$ is not hydrido or alkyl when $R^2$ is haloalkyl;

or a pharmaceutically-acceptable salt thereof.

2. Compound of claim 1 wherein $R^1$ is sulfamyl; wherein $R^2$ is selected from hydrido, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N, N-dialkylsulfamyl, N-alkyl-N-arylsulfamyl and heterocyclic; wherein $R^3$ is selected from alkyl, halo, haloalkyl, cyano, nitro, formyl, carboxyl, alkoxycarbonyl, carboxyalkyl, alkoxycarbonylalkyl, amidino, cyanoamidino, amido, alkoxy, amidoalkyl, N-monoalkylamido, N-monoarylamido, N,N-dialkylamido, N-alkyl-N-arylamido, alkylcarbonyl, alkylcarbonylalkyl, hydroxyalkyl, alkylthio, alkylsulfinyl, alkylsulfonyl, N-alkylsulfamyl, N-arylsulfamyl, arylsulfonyl, N,N-dialkylsulfamyl, N-alkyl-N-arylsulfamyl, heterocyclic, heterocycloalkyl and aralkyl; and wherein $R^4$ is selected from aryl, cycloalkyl, cycloalkenyl and heterocyclic; wherein $R^4$ is optionally substituted at a substitutable position with one or more radicals selected from halo, alkylthio, alkylsulfinyl, alkyl, alkylsulfonyl, cyano, carboxyl, alkoxycarbonyl, amido, N-monoalkylamido, N-monoarylamido, N,N-dialkylamido, N-alkyl-N-arylamido, haloalkyl, hydroxyl, alkoxy, hydroxyalkyl, haloalkoxy, sulfamyl, N-alkylsulfamyl, amino, N-alkylamino, N, N-dialkylamino, heterocyclic, nitro and acylamino; or a pharmaceutically-acceptable salt thereof.

3. Compound of claim 2 wherein $R^2$ is hydrido or haloalkyl; wherein $R^3$ is selected from alkyl, halo, carboxyalkyl, N-monoalkyl-N-hydroxyamido, N-monoalkyl-N-hydroxyamidoalkyl and N-monoalkylamido; and wherein $R^4$ is aryl optionally substituted at a substitutable position with halo; or a pharmaceutically-acceptable salt thereof.

4. Compound of claim 3 wherein $R^2$ is selected from hydrido, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl; wherein $R^3$ is selected from fluoro, chloro, bromo, methyl, ethyl, propyl, isopropyl, butyl, N-methylamido, N-ethylamido, N-isopropylamido, N-propylamido, N-butylamido, N-isobutylamido, N-tertbutylamido, N-pentylamido, N-cyclohexylamido, N-cyclopentylamido, carboxypropyl, carboxymethyl, carboxyethyl, N-methyl-N-hydroxyamido, N-methyl-N-hydroxyamidomethyl, N-methyl-N-hydroxyamidoethyl and N-methyl-N-hydroxyamidopropyl; and wherein $R^4$ is phenyl optionally substituted at a substitutable position with one or more radicals selected from fluoro, chloro and bromo; or a pharmaceutically-acceptable salt thereof.

5. Compound of claim 4 selected-from compounds, and their pharmaceutically acceptable salts, of the group consisting of 4-[5-(4-bromophenyl)-3-(cyano)-1H-pyrazol-1-yl]benzenesulfonamide;

4-[5-(4-nitrophenyl)-3-(cyano)-1H-pyrazol-1-yl]benzenesulfonamide;

1-[4-(aminosulfonyl)phenyl]-5-(4-bromophenyl)-1H-pyrazole-3-carboxamide;

methyl-1-[4-(aminosulfonyl)phenyl]-5-(4-aminophenyl)-
1H-pyrazole-3-carboxylate
ethyl-1-[4-(aminosulfonyl)phenyl]-5-(4-chlorophenyl)-1H-
pyrazole-3-carboxylate;
1-[4-(aminosulfonyl)phenyl]-5-(4-chlorophenyl)-1H-pyra-
zole-3-carboxamide;
4-[5-phenyl-3-(3 -hydroxypropyl)-1H-pyrazol-1-yl]benze-
nesulfonamide;
N-phenyl-1-[4-(aminosulfonyl)phenyl]-5-(4-fluorophenyl)-
1H-pyrazole-3-carboxamide;
N-[4-methoxyphenyl]-1-[4-(aminosulfonyl)phenyl]-5-(4-
fluorophenyl)-1H-pyrazole-3-carboxamide;
N-[3-fluorophenyl]-1-[4-(aminosulfonyl)phenyl]-5-(4-fluo-
rophenyl)-1H-pyrazole-3- carboxamide;
N-[3-chlorophenyl]-1-[4-(aminosulfonyl)phenyl]-5-(4-fluo-
rophenyl)-1H-pyrazole-3- carboxamide
N-[4-methylphenyl]-1-[4-(aminosulfonyl)phenyl]-5-(4-
fluorophenyl)-1H-pyrazole-3-carboxamide;
4-[5-(4-fluorophenyl)-3-(3-hydroxypropyl)-1H-pyrazol-1-
yl]benzenesulfonamide;
1-[4-(aminosulfonyl)phenyl]-5-(4-fluorophenyl)-1H-pyra-
zole-3-propanoic acid;
4-[5-(4-chlorophenyl)-3-(chloro)-1H-pyrazol-1-yl]benzene-
sulfonamide;
4-[5-(4-chlorophenyl)-3-(bromo)-1H-pyrazol-1-yl]benzene-
sulfonamide;
4-[5-(4-chlorophenyl)-3-(fluoro)-1H-pyrazol-1-yl]benzene-
sulfonamide;
methyl-1-[4-(aminosulfonyl)phenyl]-5-(4-chlorophenyl)-
1H-pyrazole-3-carboxylate;
4-[5-(4-chlorophenyl)-3-(cyano)-1H-pyrazol-1-yl]benzene-
sulfonamide;
N,N-dimethyl-1-[4-(aminosulfonyl)phenyl]-5-(4-chlo-
rophenyl)-1H-pyrazole-3-carboxamide;
N-methyl-1-[4-(aminosulfonyl)phenyl]-5-(4-chlorophenyl)-
1H-pyrazole-3-carboxamide;
N-methyl-N-ethyl-1-[4-(aminosulfonyl)phenyl]-5-(4-chlo-
rophenyl)-1H-pyrazole-3-carboxamide;
N-phenyl-1-[4-(aminosulfonyl)phenyl]-5-(4-chlorophenyl)-
1H-pyrazole-3-carboxamide;
N-methyl-N-phenyl-1-[4-(aminosulfonyl)phenyl]-5-(4-
chlorophenyl)-1H-pyrazole-3-carboxamide;
4-[5-(4-chlorophenyl)-3-(nitro)-1H-pyrazol-1-yl]benzene-
sulfonamide;
4-[5-(4-chlorophenyl)-3-(amidino)-1H-pyrazol-1-yl]benze-
nesulfonamide;
4-[5-(4-chlorophenyl)-3-(methylsulfonyl)-1H-pyrazol-1-yl]
benzenesulfonamide;
4-[5-(4-chlorophenyl)-3-(methylsulfamyl)-1H-pyrazol-1-
yl]benzenesulfonamide;
4-[5-(4-chlorophenyl)-3-(trifluoromethyl)-4-chloro-1H-
pyrazol-1-yl]benzenesulfonamide;
4-[5-(4- chlorophenyl)-4-chloro-1H-pyrazol-1-yl]benzene-
sulfonamide;
4-[5-(4-chlorophenyl)-3-(trifluoromethyl)-4-fluoro-1H-
pyrazol-1-yl]benzenesulfonamide;
4-[5-(4-fluorophenyl)-3-chloro-1H-pyrazol-1-yl]benzene-
sulfonamide;
N-methyl-N-hydroxy-1-[4-(aminosulfonyl)phenyl]-5-(4-
fluorophenyl)-3-(trifluoromethyl)-1H -pyrazole-4-ethana-
mide;
1-[4-(aminosulfonyl)phenyl]-5-(4-fluorophenyl)-3-(trifluo-
romethyl) -1H-pyrazole-4-acetic acid; and
N-methyl-1-[4-(aminosulfonyl)phenyl]-5-(4-fluorophenyl)-
3-(trifluoromethyl)-1H-pyrazole-4-carboxamide.

6. A compound of Formula II

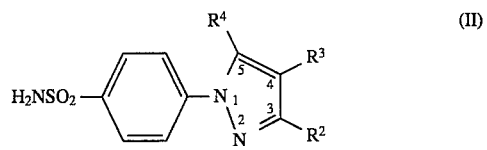

wherein $R^2$ is selected from hydrido, haloalkyl, alkoxy-
carbonyl, cyano, amido, arylamido, carboxyalkyl and
hydroxyalkyl; wherein $R^3$ is hydrido or halo; and
wherein $R^4$ is selected from aryl, cycloalkyl, cycloalk-
enyl and heterocyclic; wherein $R^4$ is optionally substi-
tuted at a substitutable position with one or more
radicals selected from halo, alkylthio, alkylsulfonyl,
cyano, nitro, haloalkyl, alkyl, hydrido, alkoxy,
haloalkoxy, sulfamyl, heterocyclic and amino; pro-
vided $R^3$ is not hydrido when $R^2$ is haloalkyl; or a
pharmaceutically-acceptable salt thereof.

7. Compound of claim 6 wherein $R^2$ is selected from
hydrido, fluoromethyl, difluoromethyl, trifluoromethyl,
chloromethyl, dichloromethyl, trichloromethyl, pentafluoro-
ethyl, heptafluoropropyl, difluorochloromethyl, dichlorof-
luoromethyl, difluoroethyl, difluoropropyl, dichloroethyl,
dichloropropyl, cyano, methoxycarbonyl, ethoxycarbonyl,
isopropoxycarbonyl, tert-butoxycarbonyl, propoxycarbonyl,
butoxycarbonyl, isobutoxycarbonyl, pentoxycarbonyl,
amido, N-phenylamido, N-(3-fluorophenyl)amido, N-(4-
methylphenyl)amido, N-(3-chlorophenyl)amido, N-(4-
methoxyphenyl)amido, 2-pyridylamido, hydroxypropyl,
hydroxymethyl, hydroxyethyl, carboxypropyl, carboxym-
ethyl and carboxyethyl; wherein $R^3$ is selected from
hydrido, fluoro, chloro, iodo and bromo; and wherein $R^4$ is
selected from phenyl, biphenyl, pyrazinyl, cyclohexyl,
cyclohexenyl and thienyl; wherein $R^4$ is optionally substi-
tuted at a substitutable position with one or more radicals
selected from chloro, bromo, fluoro, methylthio, methylsul-
fonyl, morpholinyl, amino, nitro, methyl, ethyl, propyl,
isopropyl, butyl, methoxy, ethoxy, propoxy, butoxy, trifluo-
romethoxy, trifluoroethoxy, fluoromethyl, difluoromethyl,
trifluoromethyl, chloromethyl, dichloromethyl, trichlorom-
ethyl, pentafluoroethyl, heptafluoropropyl, difluorochlorom-
ethyl, dichlorofluoromethyl, difluoroethyl, difluoropropyl,
dichloroethyl and dichloropropyl; or a pharmaceutically-
acceptable salt thereof.

8. Compound of claim 7 selected from compounds, and
their pharmaceutically-acceptable salts, of the group con-
sisting of
4-[5-(4-chlorophenyl)-4-chloro-1H-pyrazol-1-yl]benzene-
sulfonamide;
4-[5-(4-bromophenyl)-3-(cyano)-1H-pyrazol-1-yl]benzene-
sulfonamide;
4-[5-(4-nitrophenyl)-3-(cyano)-1H-pyrazol-1-yl]benzene-
sulfonamide;
1-[4-(aminosulfonyl)phenyl]-5-(4-bromophenyl)-1H-pyra-
zole-3-carboxamide;
methyl-1-[4-(aminosulfonyl)phenyl]-5-(4-aminophenyl)-
1H-pyrazole-3-carboxylate;
ethyl-1-[4-(aminosulfonyl)phenyl]-5-(4-chlorophenyl)-1H-
pyrazole-3-carboxylate;
1-[4-(aminosulfonyl)phenyl]-5-(4-chlorophenyl)-1H-pyra-
zole-3-carboxamide;
4-[5-phenyl-3-(3-hydroxypropyl)-1H-pyrazol-1-yl]benze-
nesulfonamide;
N-phenyl-1-[4-(aminosulfonyl)phenyl]-5-(4-fluorophenyl)-
1H-pyrazole-3-carboxamide;
N-[4-methoxyphenyl]-1-[4-(aminosulfonyl)phenyl]-5-(4-
fluorophenyl)-1H- pyrazole-3-carboxamide;

N-[3-fluorophenyl]-1-[4-(aminosulfonyl)phenyl]-5-(4-fluorophenyl)-1H-pyrazole-3-carboxamide;

N-[3-chlorophenyl]-1-[4-(aminosulfonyl)phenyl]-5-(4-fluorophenyl)-1H-pyrazole-3-carboxamide;

N-[4-methylphenyl]-1-[4-(aminosulfonyl)phenyl]-5-(4-fluorophenyl)-1H-pyrazole-3-carboxamide;

4-[5-(4-fluorophenyl)-3-(3-hydroxypropyl)-1H-pyrazol-1-yl]benzenesulfonamide; and 1-[4-(aminosulfonyl)phenyl]-5-(4-fluorophenyl)-1H-pyrazole-3-propanoic acid.

* * * * *